US010729600B2

(12) United States Patent
Bewick-Sonntag et al.

(10) Patent No.: US 10,729,600 B2
(45) Date of Patent: Aug. 4, 2020

(54) ABSORBENT STRUCTURE

(71) Applicant: The Procter & Gamble Company, Cincinnati, OH (US)

(72) Inventors: Christopher Philip Bewick-Sonntag, Cincinnati, OH (US); Clint Adam Morrow, Union, KY (US); Wade Monroe Hubbard, Jr., Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 426 days.

(21) Appl. No.: 15/343,989

(22) Filed: Nov. 4, 2016

(65) Prior Publication Data

US 2017/0071795 A1 Mar. 16, 2017

Related U.S. Application Data

(60) Provisional application No. 62/251,064, filed on Nov. 4, 2015, provisional application No. 62/186,814, filed on Jun. 30, 2015.

(51) Int. Cl.
*A61F 13/15* (2006.01)
*A61F 13/534* (2006.01)
*A61F 13/53* (2006.01)

(52) U.S. Cl.
CPC .... *A61F 13/534* (2013.01); *A61F 2013/1539* (2013.01); *A61F 2013/15308* (2013.01); *A61F 2013/15325* (2013.01); *A61F 2013/530007* (2013.01); *A61F 2013/530379* (2013.01); *A61F 2013/530817* (2013.01)

(58) Field of Classification Search
CPC .......... A61F 13/534; A61F 2013/15308; A61F 2013/15325; A61F 2013/1539; A61F 2013/530007; A61F 2013/530379; A61F 2013/530817
See application file for complete search history.

(56) References Cited

U.S. PATENT DOCUMENTS

| | | | |
|---|---|---|---|
| 1,035,758 A | 7/1919 | Thompson, Jr. et al. |
| 3,122,142 A | 2/1964 | Crowe, Jr. |
| 3,274,046 A | 9/1966 | Shannon et al. |
| 3,546,055 A | 12/1970 | Spertus |
| 3,617,594 A | 11/1971 | Willhy |
| 3,669,823 A | 6/1972 | Wood |

(Continued)

FOREIGN PATENT DOCUMENTS

| | | |
|---|---|---|
| CA | 2250138 | 3/1997 |
| EP | 0278476 | 2/1988 |

(Continued)

OTHER PUBLICATIONS

PCT International Search Report, PCT/US2016/060581, dated Feb. 3, 2017, 13 pages.

(Continued)

*Primary Examiner* — Jacqueline F Stephens
(74) *Attorney, Agent, or Firm* — William E. Gallagher

(57) ABSTRACT

An absorbent structure comprising one or more absorbent layers wherein the absorbent structure exhibits a first cycle Peak Force compression between about 30 grams and about 150 grams. The absorbent structure further exhibits a fifth cycle dry recovery energy between 0.1 mJ and 2.8 mJ.

17 Claims, 15 Drawing Sheets

(56) References Cited

U.S. PATENT DOCUMENTS

| | | |
|---|---|---|
| 3,804,700 A | 4/1974 | Hoey |
| 3,815,601 A | 6/1974 | Schaefer |
| 3,884,000 A | 5/1975 | Faleij |
| 3,982,374 A | 9/1976 | Schaefer |
| 3,994,298 A | 11/1976 | Des Marais |
| 4,026,292 A | 5/1977 | Hutchins et al. |
| 4,055,184 A | 10/1977 | Karami |
| 4,061,145 A | 12/1977 | DesMarais |
| 4,096,303 A | 6/1978 | Doerfling |
| 4,357,386 A | 11/1982 | Luciano |
| 4,450,833 A | 5/1984 | Brooks |
| 4,473,611 A | 9/1984 | Haq |
| 4,535,021 A | 8/1985 | Friedrich |
| 4,606,958 A | 8/1986 | Haq et al. |
| 4,664,662 A | 5/1987 | Webster |
| 4,689,258 A | 8/1987 | Slosberg |
| 4,740,700 A | 4/1988 | Shaham |
| 4,758,466 A | 7/1988 | Dabi et al. |
| 4,865,596 A | 9/1989 | Weisman et al. |
| 5,147,345 A | 9/1992 | Young et al. |
| 5,160,345 A | 11/1992 | Bragg |
| 5,175,046 A | 12/1992 | Nguyen |
| 5,221,726 A | 6/1993 | Dabi et al. |
| 5,234,423 A | 8/1993 | Alemany et al. |
| 5,248,309 A | 9/1993 | Serbiak et al. |
| 5,260,345 A | 11/1993 | DesMarais et al. |
| 5,306,734 A | 4/1994 | Bass et al. |
| 5,328,935 A | 7/1994 | Van Phan et al. |
| 5,331,015 A | 7/1994 | DesMarais et al. |
| 5,338,766 A | 8/1994 | Phan et al. |
| 5,387,207 A * | 2/1995 | Dyer ............... A61F 5/4401 521/64 |
| 5,454,801 A | 10/1995 | Lauritzen |
| 5,487,736 A | 1/1996 | Van Phan |
| 5,536,264 A | 7/1996 | Hsueh et al. |
| 5,560,878 A | 10/1996 | Dragoo et al. |
| 5,713,881 A | 2/1998 | Rezai |
| 5,722,482 A | 3/1998 | Buckley |
| 5,817,704 A | 10/1998 | Shiveley et al. |
| 5,868,724 A | 2/1999 | Dierckes, Jr. et al. |
| 5,869,171 A * | 2/1999 | Shiveley ............ A61F 13/53 428/304.4 |
| 5,948,829 A | 9/1999 | Wallajapet et al. |
| 5,962,068 A | 10/1999 | Tsuchiya et al. |
| 6,083,211 A | 7/2000 | DesMarais |
| 6,103,645 A | 8/2000 | Chang et al. |
| 6,107,538 A | 8/2000 | Young et al. |
| 6,132,803 A | 10/2000 | Kelly et al. |
| 6,174,929 B1 | 1/2001 | Hahnle et al. |
| 6,183,587 B1 | 2/2001 | McFall et al. |
| 6,203,654 B1 | 3/2001 | McFall et al. |
| 6,261,679 B1 | 7/2001 | Chen et al. |
| 6,277,104 B1 | 8/2001 | Lasko et al. |
| 6,316,688 B1 | 11/2001 | Hammons et al. |
| 6,372,953 B1 * | 4/2002 | Young ............... A43B 1/0036 604/369 |
| 6,410,820 B1 | 6/2002 | McFall et al. |
| 6,426,445 B1 | 7/2002 | Young et al. |
| 6,455,600 B1 | 9/2002 | Hahnle et al. |
| 6,475,199 B1 | 11/2002 | Gann et al. |
| 6,525,106 B1 | 2/2003 | DesMarais et al. |
| 6,551,295 B1 | 4/2003 | Schmidt et al. |
| 6,582,411 B1 | 6/2003 | Carstens et al. |
| 6,590,136 B1 | 7/2003 | Young et al. |
| 6,603,054 B2 | 8/2003 | Chen et al. |
| 6,642,430 B1 | 11/2003 | Busam et al. |
| 6,657,101 B1 | 12/2003 | Malmgren et al. |
| 6,664,439 B1 | 12/2003 | Arndt et al. |
| 6,673,057 B1 | 1/2004 | Ehrnsperger et al. |
| 6,673,981 B1 | 1/2004 | Strömbom et al. |
| 6,706,775 B2 | 3/2004 | Hermann et al. |
| 6,713,661 B1 | 3/2004 | Arndt et al. |
| 6,720,471 B1 | 4/2004 | Arndt et al. |
| 6,800,666 B2 | 10/2004 | Hahnle et al. |
| 6,811,842 B1 | 11/2004 | Ehrnsperger et al. |
| 6,943,200 B1 | 9/2005 | Corrand et al. |
| 6,969,548 B1 | 11/2005 | Goldfine |
| 6,989,005 B1 | 1/2006 | LaVon et al. |
| 7,056,404 B2 | 6/2006 | McFall et al. |
| 7,189,888 B2 | 3/2007 | Wang et al. |
| 7,235,708 B2 | 6/2007 | Guidotti et al. |
| 7,285,576 B2 | 10/2007 | Hyde et al. |
| 7,462,756 B2 | 12/2008 | Malowaniec |
| 7,850,672 B2 | 12/2010 | Guidotti et al. |
| 7,935,207 B2 | 5/2011 | Zhao et al. |
| 8,143,472 B1 | 3/2012 | Bragd et al. |
| 8,207,393 B2 | 6/2012 | Bach |
| 8,426,670 B2 | 4/2013 | Nagasuna et al. |
| 8,707,717 B2 | 4/2014 | Fox et al. |
| 8,708,723 B2 | 4/2014 | Stoltz |
| 8,906,404 B2 | 12/2014 | Wellings |
| 1,004,589 A1 | 8/2018 | Hubbard, Jr. |
| 2001/0024716 A1 | 9/2001 | Chen et al. |
| 2001/0041876 A1 | 11/2001 | Creagan et al. |
| 2001/0047456 A1 | 11/2001 | Schrobenhauzer et al. |
| 2002/0034911 A1 | 3/2002 | Tsuchiya et al. |
| 2002/0095132 A1 | 7/2002 | Ashton et al. |
| 2002/0132106 A1 | 9/2002 | Dyer et al. |
| 2003/0084788 A1 | 5/2003 | Fraser |
| 2003/0134918 A1 | 7/2003 | Ko et al. |
| 2003/0181884 A1 | 9/2003 | Carstens et al. |
| 2003/0191204 A1 | 10/2003 | Hermann et al. |
| 2003/0211248 A1 | 11/2003 | Ko et al. |
| 2004/0054341 A1 | 3/2004 | Kellenberger et al. |
| 2004/0054342 A1 | 3/2004 | Newbill |
| 2004/0121905 A1 | 6/2004 | Ranganathan et al. |
| 2004/0193129 A1 | 9/2004 | Guidotti et al. |
| 2004/0204554 A1 | 10/2004 | Ko et al. |
| 2004/0214961 A1 | 10/2004 | Gartner et al. |
| 2005/0087292 A1 | 4/2005 | McFall et al. |
| 2005/0136224 A1 | 6/2005 | Nickel et al. |
| 2005/0250866 A1 | 11/2005 | Champ et al. |
| 2005/0266230 A1 | 12/2005 | Hill et al. |
| 2006/0189240 A1 | 8/2006 | Taylor et al. |
| 2008/0076844 A1 | 3/2008 | VanSumeren et al. |
| 2008/0221538 A1 | 9/2008 | Zhao et al. |
| 2009/0270827 A1 | 10/2009 | Gundersen et al. |
| 2010/0307665 A1 | 12/2010 | McCutchen |
| 2011/0070423 A1 | 3/2011 | Jayakody et al. |
| 2012/0001122 A1 | 1/2012 | Wattelbled |
| 2012/0201806 A1 | 8/2012 | Silverstein et al. |
| 2012/0237606 A1 | 9/2012 | Wellings |
| 2012/0296296 A1 | 11/2012 | DiCintio et al. |
| 2012/0302440 A1 | 11/2012 | Theliander et al. |
| 2013/0079741 A1 | 3/2013 | Nakashita et al. |
| 2014/0228796 A1 | 8/2014 | Burvall et al. |
| 2014/0295134 A1 | 10/2014 | Wood et al. |
| 2014/0295135 A1 | 10/2014 | Thompson, Jr. et al. |
| 2015/0119837 A1 | 4/2015 | Thompson, Jr. et al. |
| 2015/0245957 A1 | 9/2015 | Hashino et al. |
| 2015/0313770 A1 | 11/2015 | Hubbard, Jr. et al. |
| 2015/0335498 A1 | 11/2015 | Hubbard, Jr. et al. |
| 2015/0374876 A1 | 12/2015 | Hubbard, Jr. |

FOREIGN PATENT DOCUMENTS

| | | |
|---|---|---|
| EP | 0794751 | 11/1995 |
| EP | 1061966 | 3/1999 |
| EP | 1267769 | 1/2003 |
| EP | 1605881 | 1/2004 |
| EP | 1139951 | 10/2004 |
| EP | 1358894 | 11/2013 |
| GB | 1570485 | 7/1980 |
| GB | 2326828 | 1/1999 |
| JP | 2013180171 A | 9/2013 |
| WO | WO9611714 | 4/1996 |
| WO | WO9945878 | 9/1999 |
| WO | WO9947184 | 9/1999 |
| WO | WO9955269 | 11/1999 |
| WO | WO0000138 | 1/2000 |
| WO | WO0000136 | 12/2000 |
| WO | WO0059438 | 12/2000 |
| WO | WO0078369 | 12/2000 |
| WO | WO2001068022 | 9/2001 |

(56) References Cited

FOREIGN PATENT DOCUMENTS

| WO | WO2003026707 | 10/2003 |
| WO | WO2004084784 | 10/2004 |
| WO | WO2004084785 | 10/2004 |
| WO | WO2013180937 | 12/2013 |

OTHER PUBLICATIONS

All Office Actions, U.S. Appl. No. 14/704,110.
All Office Actions, U.S. Appl. No. 14/715,984.
All Office Actions, U.S. Appl. No. 14/750,596.
All Office Actions, U.S. Appl. No. 15/084,902.
All Office Actions, U.S. Appl. No. 15/344,050.
All Office Actions, U.S. Appl. No. 15/344,090.
All Office Actions, U.S. Appl. No. 15/344,117.
All Office Actions, U.S. Appl. No. 15/344,177.
All Office Actions, U.S. Appl. No 15/344,292.

* cited by examiner

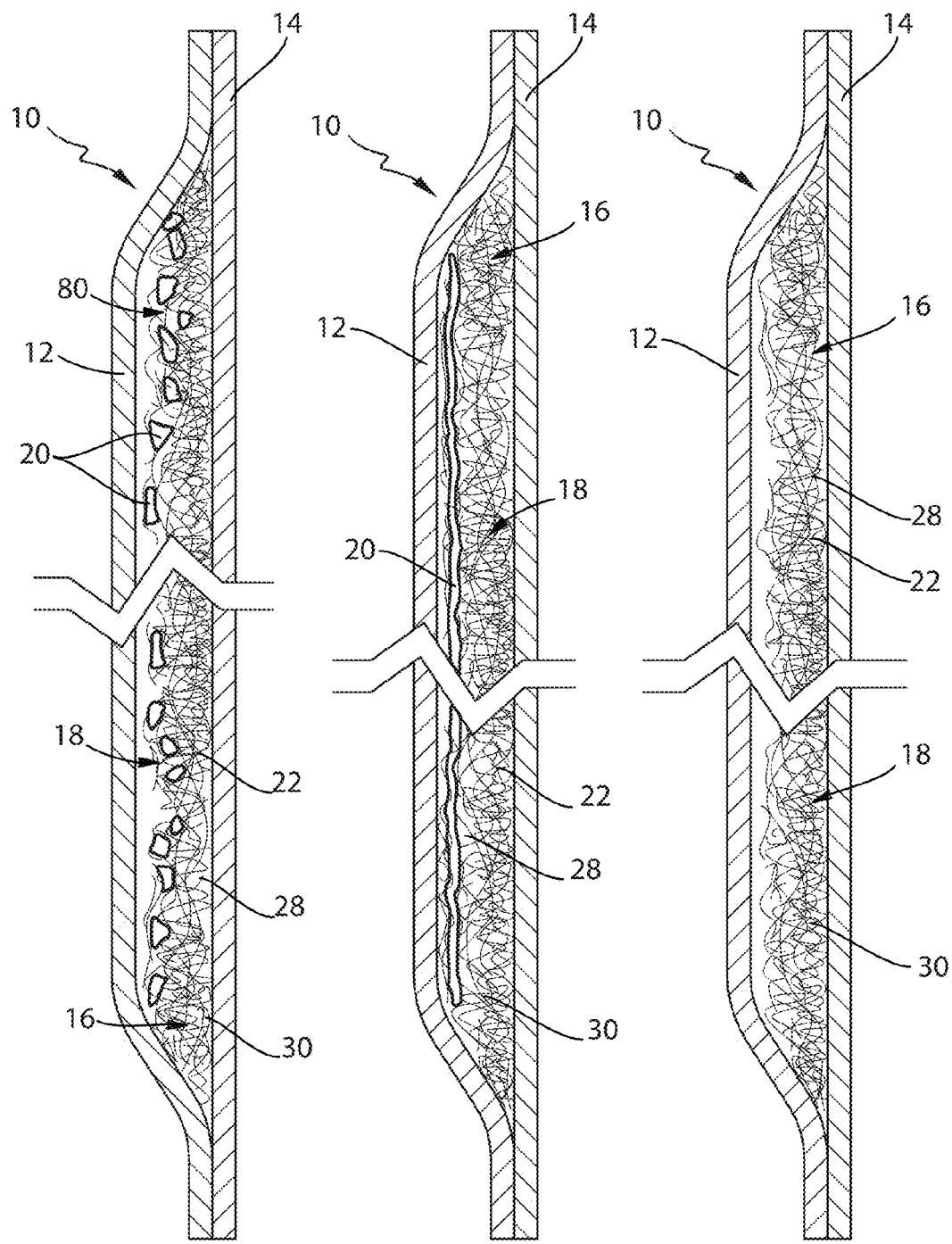

US 10,729,600 B2

ABSORBENT STRUCTURE

FIELD OF THE INVENTION

The present invention relates to absorbent structures useful in absorbent articles such as diapers, incontinent briefs, training pants, diaper holders and liners, sanitary hygiene garments, and the like. Specifically, the present invention relates to an absorbent structure that exhibits desirable consumer properties.

BACKGROUND OF THE INVENTION

Absorbent articles for the absorption of fluids aim to be comfortable to the consumer. This traditionally represents the use of thinner materials while increasing absorption. Increased comfort may also be achieved through the use of channels and cuts into the absorbent core to create flexible zones that may include removing parts of the absorbent core. A goal of increased comfort is to create an absorbent article that is garment-like to the consumer while still protecting the consumer.

Traditionally, as a consumer wears an absorbent product and fluid enters the product the structural properties of the absorbent core and product change and degrade. This is because, the material will traditionally either lose its structural integrity or become less flexible, bunch together and unable to retain its shape as it absorbs the fluid, dependent upon the composition of the absorbent article. Further, many absorbent products may become more noticeable, with wearing, to the consumer making them aware that they are using an absorbent product and that the product is changing and may no longer function as well as it originally did.

The loss of structural integrity or loss of flexibility or inability to maintain shape and compression recovery leads to a tradeoff between comfort and protection. Absorbent core structures that loss structural integrity tend to lose wet resiliency leading to a loss of consumer confidence in the products ability to protect and absorb. Absorbent cores that lose flexibility due to their composition may become uncomfortable as they are no longer garment like. Hence, there exists a need to create an absorbent core that balances comfort with protection such that it may handle subsequent insults without the consumer feeling that the product will not protect them and/or be uncomfortable to use.

The response of an absorbent structure (or article) to body induced mechanical compression while wearing is referred to as its bunched compression response. Bunched compression can be an important factor with regard to the overall comfort associated with wearing an absorbent article. Ideally measuring the Bunched compression response would allow one to determine peak forces required to compress an absorbent structure as well as determine the stored energy available to drive a products shape recovery or "Energy of Recovery" following a compression of the article when in use With regard to bunched compression of an absorbent structure during wear, it can be difficult to predict all the possible movements and positions that the consumer will make while using the absorbent article. These can impact whether the consumer feels the absorbent article and/or finds the absorbent article comfortable. It is therefore desired to develop a method for evaluating the bunched compression response of an absorbent article or portions of an absorbent article or an absorbent core structure that provides an indication as to the compression of the absorbent article during wear.

Further, there exists a need to create an absorbent structure that is sufficiently flexible before use and is still capable of maintaining its structural integrity after multiple insults as exhibited by the absorbent structure's recovery energy after multiple test cycles.

Further, there exists a need to create a method for the creation of an absorbent structure that becomes or maintains its flexibility while absorbing the fluids therefore allowing one to model the product according to the consumer's needs.

SUMMARY OF THE INVENTION

An absorbent structure comprising one or more absorbent layers wherein the absorbent structure exhibits a first cycle Peak Force compression between about 30 grams and about 150 grams is described. The absorbent structure further exhibits a fifth cycle dry recovery energy between 0.1 mJ and 2.8 mJ.

An absorbent structure comprising one or more absorbent layers wherein the absorbent structure exhibits a first cycle Peak Force compression between about 30 grams and about 150 grams is described. The absorbent structure further exhibits a fifth cycle dry recovery energy between 0.1 mJ and 2.8 mJ and a fifth cycle wet recovery energy between 0.6 mJ and 5.0 mJ.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 5 is a cross section view of the absorbent article of FIG. 4 taken along line 5-5.

FIG. 6 is a cross section view of the absorbent article of FIG. 4 taken along line 6-6.

FIG. 7 is a cross section view of the absorbent article of FIG. 4 taken along line 7-7.

DETAILED DESCRIPTION OF THE INVENTION

Figure 1:
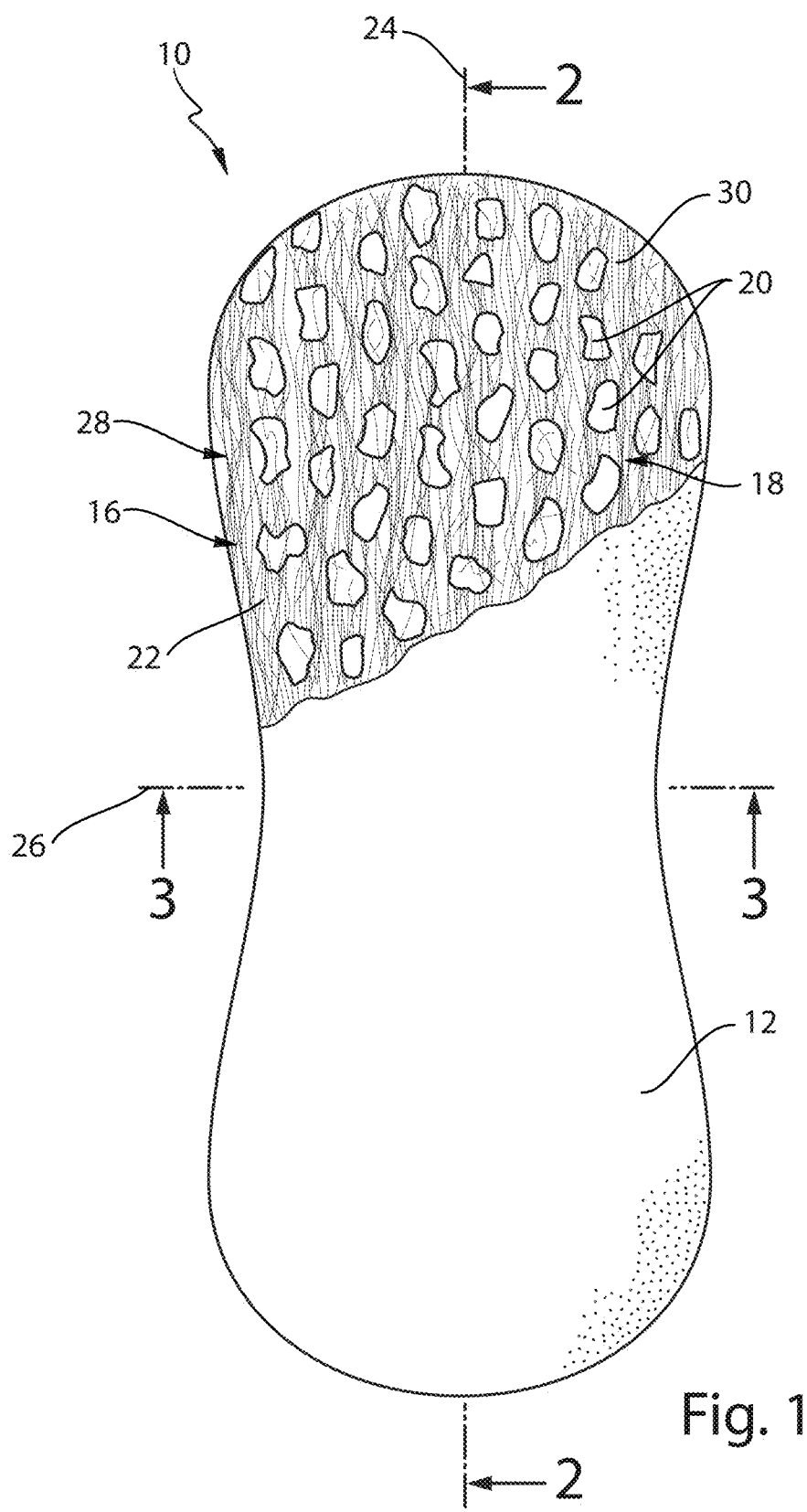
FIG. 1 is a top view of an absorbent article.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose, e.g. viscose or partially or fully acetylated cellulose derivatives (e.g. cellulose acetate or triacetate), are also considered as cellulose fibers according to the present invention.

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin, a panty liner, an adult incontinence product, a diaper, or any other product designed to absorb a bodily exudate. The absorbent structure of the present invention will be herein described in the context of a typical absorbent article, such as, for example, a sanitary napkin. Typically, such articles can comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that can be part of a fibrous structure. Fibers can be natural or synthetic. Fibers can be absorbent or non-absorbent.

A "fibrous structure" as used herein, refers to materials which can be broken into one or more fibers. A fibrous structure can be absorbent or adsorbent. A fibrous structure can exhibit capillary action as well as porosity and permeability.

As used herein, the term "immobilize" refers to the reduction or the elimination of movement or motion.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers can be solid or hollow, and they can be tri-lobal, delta-shaped, and may be fibers having capillary channels on their outer surfaces. The capillary channels can be of various cross-sectional shapes such as "U-shaped", "H-shaped", "C-shaped" and "V-shaped". One practical capillary channel fiber is T401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, electro-spinning, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in an article of the present invention can range from about 10 gsm to about 100 gsm, depending on the ultimate use of the web.

As used herein, the term "peak force" relates to an indicator of the flexibility of the absorbent structure during compression. A lower "peak force" represents a more flexible absorbent structure or absorbent product.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "recovery energy" relates to an indicator of how well an absorbent structure or absorbent product can retain or regain is original shape. More specifically, "recovery energy" is a measure of the amount of work the absorbent structure or the absorbent product will perform against the consumer's body and/or garment following compression.

Without being bound by theory, the upper limit for recovery energy should be the compressive energy i.e. a fully recovered product when removed from the consumer's body/garment. Dry recovery energy for between 1 and 20 cycles should be less than 250% the dry compressive energy of a new product.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "test cycle" refers to a cycle of the Bunched Compression test.

As used herein, a "strata" or "stratum" relates to one or more layers wherein the components within the stratum are intimately combined without the necessity of an adhesive, pressure bonds, heat welds, a combination of pressure and heat bonding, hydro-entangling, needlepunching, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft can comprise a plurality of looped, aligned fibers extending outwardly from the surface of the web. Each tuft can comprise a plurality of non-looped fibers that extend outwardly from the surface of the web. Each tuft can comprise a plurality of fibers which are integral extensions of the fibers of two or more integrated nonwoven webs.

As used herein, a "usage cycle" relates to the duration of use of the absorbent structure as it transitions from a dry state to a saturated wet state.

While particular embodiments of the present invention have been illustrated and described, it would be obvious to those skilled in the art that various other changes and modifications can be made without departing from the spirit and scope of the invention.

GENERAL SUMMARY

The present invention relates to an absorbent structure that is flexible and maintains its resiliency while in use. The absorbent structure also increases in volume by less than 250% during the usage cycle, therefore achieving a flexible product that maintains resiliency, bulk, and comfort during a usage cycle.

The absorbent structure may comprise one or more absorbent layers. The absorbent structure may be a heterogeneous mass. In an embodiment, the absorbent core structure is a two layer system wherein the upper layer is heterogeneous mass layer comprising one or more enrobeable elements and one or more discrete open-cell foam pieces. The upper layer heterogeneous mass layer may be a stratum as defined above. The lower layer is an absorbent layer that comprises superabsorbent polymer. The absorbent core structure may comprise additional layers below the absorbent layer that comprises superabsorbent polymer.

The absorbent core structure may comprise a heterogeneous mass layer as those described in U.S. patent application No. 61/988,565, filed May 5, 2014; U.S. patent application No. 62/115,921, filed Feb. 13, 2015; or U.S. patent application No. 62/018,212. The heterogeneous mass layer has a depth, a width, and a height.

The absorbent structure may comprise an absorbent core or absorbent core elements such 20 as those described in U.S. Pat. No. 8,263,820 issued Sep. 11, 2012 and U.S. Pat. No. 8,124,827 issued Feb. 28, 2012.

The absorbent structure may have a substrate layer. The substrate layer of the absorbent structure may advantageously comprise a fibrous material substantially free of cellulose fibers. By saying that a layer of the absorbent core is "substantially free" of cellulose fibers, it is meant in the context of the present invention that the layer should not comprise any significant amount of cellulose fibers within its inner structure. While cellulose fibers which may be present at an outer surface of the specified layer, for example at the interface between the specified layer and an adjacent one, which could be for example an outer layer wrapping the core 28, in some cases may accidentally and slightly penetrate the structure of the specified layer, such shall not be considered significant. Significant amounts may correspond to less than 10% by weight, less than 5% by weight, less than 3% by weight, or less than 1% by weight, based on the dry weight of the specified layer of the absorbent core. The substrate layer 100 may also have a basis weight from 25 g/m2 to 120 g/m2, or from 35 g/m2 to 90 g/m2.

The absorbent structure may have a thermoplastic layer of thermoplastic material. The thermoplastic material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer may have typically a molecular weight (Mw) of more than 10,000 and a glass transition temperature (Tg) usually below room temperature. Typical concentrations of the polymer in a hot melt are in the range of 20-40% by weight. A wide variety of thermoplastic polymers may be suitable for use in the present invention. Such thermoplastic polymers can be typically water insensitive. Exemplary polymers can be (styrenic) block copolymers including A-B-A triblock structures, A-B diblock structures and (A-B)n radial block copolymer structures wherein the A blocks can be non-elastomeric polymer blocks, typically comprising polystyrene, and the B blocks can be unsaturated conjugated diene or (partly) hydrogenated versions of such. The B block can be typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable can be amorphous polyolefins or amorphous polyalphaolefins (APAO) which are homopolymers, copolymers or terpolymers of C2 to C8 alphaolefins.

The resin can typically have a Mw below 5,000 and a Tg usually above room temperature, typical concentrations of the resin in a hot melt can be in the range of 30-60%. The plasticizer has a low Mw of typically less than 1,000 and a Tg below room temperature, a typical concentration is 0-15%.

The thermoplastic material, typically a hotmelt adhesive, can be present in the form of fibers throughout the core, being provided with known means, i.e. the adhesive can be fiberized. Typically, the fibers can have an average thickness of 1-100 micrometer and an average length of 5 mm to 50 cm. In particular the layer of thermoplastic material, typically e.g. a hot melt adhesive, can be provided such as to comprise a net-like structure.

To improve the adhesiveness of the thermoplastic material to the substrate layer or to any other layer, in particular any other non-woven layer, such layers may be pre-treated with an auxiliary adhesive.

The absorbent structure may have absorbent polymer material. Without wishing to be bound by theory it is believed that such material, even in the swollen state, i.e. when liquid has been absorbed, does not substantially obstruct the liquid flow throughout the material, particularly when further the permeability of said material, as expressed by the saline flow conductivity (SFC) of the absorbent polymer material, is greater than 10, 20, 30 or 40 SFC-units, where 1 SFC unit is 1×10−7 (cm3×s)/g. Saline flow conductivity is a parameter well recognized in the art and is to be measured in accordance with the test disclosed in EP 752 892 B.

The absorbent structure may be a heterogeneous mass. The heterogeneous mass has a depth, a width, and a height. The absorbent structure may be used as any part of an absorbent article including, for example, a part of an absorbent core, as an absorbent core, and/or as a topsheet for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. The absorbent structure may be used in any product utilized to absorb and retain a fluid including surface wipes. The absorbent structure may be used as a paper towel. Exemplary absorbent articles in the context of the present invention are disposable absorbent articles.

The absorbent structure may be a heterogeneous mass comprising enrobeable elements and one or more portions of foam pieces. The discrete portions of foam pieces are open-celled foam. The foam may be a High Internal Phase Emulsion (HIPE) foam.

The absorbent structure may be an absorbent core for an absorbent article wherein the absorbent core comprises a heterogeneous mass comprising fibers and one or more discrete portions of foam that are immobilized in the heterogeneous mass.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The present invention relates to an absorbent structure that contains one or more discrete open-cell foam pieces foams that are integrated into a heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass may have void space found between the enrobeable elements, between the enrobeable elements and the enrobed elements, and between enrobed elements. The void space may contain a gas such as air. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the, such as for example, between 20 g/g and 190 g/g of the heterogeneous mass, such as, for example 30 g/g, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

A discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

A discrete open-cell foam piece may be immobilized such that the discrete open-cell foam piece does not change location within the heterogeneous mass during use of the absorbent structure.

A plurality of discrete open-cell foams may be immobilized such that the discrete open-cell foam pieces do not change location within the heterogeneous mass during use of the absorbent structure.

One or more discrete foam pieces may be immobilized within the heterogeneous mass such that the one or more discrete foam pieces do not change location after being spun at 300 rotations per minute for 30 seconds.

The open-cell foam pieces may be discrete. Open-cell foam pieces are considered discrete in that they are not continuous throughout the entire heterogeneous mass. Not continuous throughout the entire heterogeneous mass represents that at any given point in the heterogeneous mass, the open-cell absorbent foam is not continuous in at least one of the cross sections of a longitudinal, a vertical, and a lateral plane of the heterogeneous mass. The absorbent foam may or may not be continuous in the lateral and the vertical planes of the cross section for a given point in the heterogeneous mass. The absorbent foam may or may not be continuous in the longitudinal and the vertical planes of the cross section for a given point in the heterogeneous mass. The absorbent foam may or may not be continuous in the longitudinal and the lateral planes of the cross section for a given point in the heterogeneous mass.

When the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. A foam piece may be surrounded by the elements that make up the enrobeable elements. A foam piece may be located on the outer perimeter of the heterogeneous mass such that only a portion of the foam piece is entangled with the elements of the heterogeneous mass.

The open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. The open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces. The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

Dependent upon the desired foam density, polymer composition, specific surface area, or pore-size (also referred to as cell size), the open-celled foam may be made with different chemical composition, physical properties, or both. For instance, dependent upon the chemical composition, an open-celled foam may have a density of 0.0010 g/cc to about 0.25 g/cc, or from 0.002 g/cc to about 0.2 g/cc, or from about 0.005 g/cc to about 0.15 g/cc, or from about 0.01 g/cc to about 0.1 g/cc, or from about 0.02 g/cc to about 0.08 g/cc, or about 0.04 g/cc.

Open-cell foam pore-sizes may range in average diameter of from 1 to 800 μm, such as, for example, between 50 and 700 μm, between 100 and 600 μm, between 200 and 500 μm, between 300 and 400 μm.

The foam pieces may have a relatively uniform cell size. For example, the average cell size on one major surface may be about the same or vary by no greater than 10% as compared to the opposing major surface. The average cell size of one major surface of the foam may differ from the opposing surface. For example, in the foaming of a thermosetting material it is not uncommon for a portion of the cells at the bottom of the cell structure to collapse resulting in a lower average cell size on one surface. The cell size may be determined based upon the method found below. The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "opencelled" if at least about 80% of the cells in the foam that are at least 1 μm in average diameter size are in fluid communication with at least one adjoining cell.

In addition to being open-celled, the foams may be sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

For example when used in certain absorbent articles, an open-cell foam may be flexible and exhibit an appropriate glass transition temperature (Tg). The Tg represents the midpoint of the transition between the glassy and rubbery states of the polymer.

The Tg of a region may be less than about 200° C. for foams used at about ambient temperature conditions, or less than about 90° C. The Tg may be less than 50° C.

The open-cell foam pieces may be distributed in any suitable manner throughout the heterogeneous mass. The open-cell foam pieces may be profiled along the vertical axis such that smaller pieces are located above larger pieces. Alternatively, the pieces may be profiled such that smaller pieces are below larger pieces. The open-cell pieces may be profiled along a vertical axis such that they alternate in size along the axis.

The open-cell foam pieces may be profiled along the longitudinal axis such that smaller pieces are located in front of larger pieces. Alternatively, the pieces may be profiled such that smaller pieces are behind larger pieces. The open-cell pieces may be profiled along a longitudinal axis such that they alternate in size along the axis. The open-cell foam pieces may be profiled along the lateral axis such the size of the pieces goes from small to large or from large to small along the lateral axis. Alternatively, the open-cell pieces may be profiled along a lateral axis such that they alternate in size along the axis.

The open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

The open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. The open-cell foam pieces may be distributed in a manner that forms a design or shape when viewed from a top planar view. The open-cell foam pieces may be distributed in a manner that forms stripes, ellipticals, squares, or any other known shape or pattern.

The distribution may be optimized dependent on the intended use of the heterogeneous mass. For example, a different distribution may be chosen for the absorption of aqueous fluids such as urine when used in a diaper or water when used in a paper towel versus for the absorption of a proteinaceous fluid such as menses. Further, the distribution may be optimized for uses such as dosing an active or to use the foam as a reinforcing element.

Different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The foam pieces may be similar in composition yet exhibit different properties. For example, using HIPE foam, some foam pieces may be thin until wet while others may have been expanded within the heterogeneous mass.

The foam pieces and enrobeable elements may be selected to complement each other. For example, a foam that exhibits high permeability with low capillarity may enrobe an element that exhibits high capillarity to wick the fluid through the heterogeneous mass. It is understood that other combinations may be possible wherein the foam pieces complement each other or wherein the foam pieces and enrobeable elements both exhibit similar properties.

Profiling may occur using more than one heterogeneous mass with each heterogeneous mass having one or more types of foam pieces. The plurality of heterogeneous masses may be layered so that the foam is profiled along any one of the longitudinal, lateral, or vertical axis based on one or more characteristics of the open-cell foam pieces for an overall product that contains the plurality of heterogeneous masses. Further, each heterogeneous mass may have a different enrobeable element to which the foam is attached. For example, a first heterogeneous mass may have foam particles enrobing a nonwoven while a second heterogeneous mass adjacent the first heterogeneous mass may have foam particles enrobing a film or one surface of a film.

The open-cell foam may be made from a polymer formula that can include any suitable thermoplastic polymer, or blend of thermoplastic polymers, or blend of thermoplastic and non-thermoplastic polymers.

Examples of polymers, or base resins, suitable for use in the foam polymer formula include styrene polymers, such as polystyrene or polystyrene copolymers or other alkenyl aromatic polymers; polyolefins including homo or copolymers of olefins, such as polyethylene, polypropylene, polybutylene, etc.; polyesters, such as polyalkylene terephthalate; and combinations thereof. A commercially available example of polystyrene resin is Dow STYRON® 685D, available from Dow Chemical Company in Midland, Mich., U.S.A.

Coagents and compatibilizers can be utilized for blending such resins. Crosslinking agents can also be employed to enhance mechanical properties, foamability and expansion. Crosslinking may be done by several means including electron beams or by chemical crosslinking agents including organic peroxides. Use of polymer side groups, incorporation of chains within the polymer structure to prevent polymer crystallization, lowering of the glass transition temperature, lowering a given polymer's molecular weight distribution, adjusting melt flow strength and viscous elastic properties including elongational viscosity of the polymer melt, block copolymerization, blending polymers, and use of polyolefin homopolymers and copolymers have all been used to improve foam flexibility and foamability. Homopolymers can be engineered with elastic and crystalline areas. Syndiotactic, atactic and isotactic polypropylenes, blends of such and other polymers can also be utilized. Suitable polyolefin resins include low, including linear low, medium and high-density polyethylene and polypropylene, which are normally made using Ziegler-Natta or Phillips catalysts and are relatively linear; generally more foamable are resins having branched polymer chains. Isotactic propylene homopolymers and blends are made using metallocene-based catalysts. Olefin elastomers are included. Ethylene and a-olefin copolymers, made using either Ziegler-Natta or a metallocene catalyst, can produce soft, flexible foam having extensibility. Polyethylene cross-linked with aolefins and various ethylene ionomer resins can also be utilized. Use of ethyl-vinyl acetate copolymers with other polyolefin-type resins can produce soft foam. Common modifiers for various polymers can also be reacted with chain groups to obtain suitable functionality. Suitable alkenyl aromatic polymers include alkenyl aromatic homopolymers and copolymers of alkenyl aromatic compounds and copolymerizable ethylenically unsaturated comonomers including minor proportions of non-alkenyl aromatic polymers and blends of such. Ionomer resins can also be utilized.

Other polymers that may be employed include natural and synthetic organic polymers including cellulosic polymers, methyl cellulose, polylactic acids, polyvinyl acids, polyacrylates, polycarbonates, starch-based polymers, polyetherimides, polyamides, polyesters, polymethylmethacrylates, and copolymer/polymer blends. Rubber-modified polymers such as styrene elastomers, styrene/butadiene copolymers, ethylene elastomers, butadiene, and polybutylene resins, ethylene-propylene rubbers, EPDM, EPM, and other rubbery homopolymers and copolymers of such can be added to enhance softness and hand. Olefin elastomers can also be utilized for such purposes. Rubbers, including natural rubber, SBR, polybutadiene, ethylene propylene terpolymers, and vulcanized rubbers, including TPVs, can also be added to improve rubber-like elasticity.

Thermoplastic foam absorbency can be enhanced by foaming with spontaneous hydrogels, commonly known as superabsorbents. Superabsorbents can include alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, carboxy-methylcellulose, isobutylene maleic anhydride copolymers, and mixtures thereof. Further suitable polymers include inorganic polymers, such as polyphosphazene, and the like. Furthermore, thermoplastic foam biodegradability and absorbency can be enhanced by foaming with cellulose-based and starch-based components such as wood and/or vegetable fibrous pulp/flour.

In addition to any of these polymers, the foam polymer formula may also, or alternatively, include diblock, triblock, tetrablock, or other multi-block thermoplastic elastomeric and/or flexible copolymers such as polyolefin-based thermoplastic elastomers including random block copolymers including ethylene a-olefin copolymers; block copolymers including hydrogenated butadiene-isoprene-butadiene block copolymers; stereoblock polypropylenes; graft copolymers, including ethylene-propylene-diene terpolymer or ethylene-propylene-diene monomer (EPDM), ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprenestyrene (SIS), styrene-butadiene-styrene (SBS), styrene (SBS) styrene-isoprene-butadiene-styrene (SIBS), styrene-ethylene/butylene-styrene (SEBS), or styrene-ethylene/propylene-styrene (SEPS), which may be obtained from Kraton Polymers of Belpre, Ohio, U.S.A., under the trade designation KRATON® elastomeric resin or from Dexco, a division of ExxonMobil Chemical Company in Houston, Tex., U.S.A., under the trade designation VECTOR® (SIS and SBS polymers) or SEBS polymers as the SEPTON® series of thermoplastic rubbers from Kuraray America, Inc. in New York, N.Y., U.S.A.; blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E.I. Du Pont de Nemours in Wilmington, Del., U.S.A., under the trade name LYCRA® polyurethane, and ESTANE® available from Noveon, Inc. in Cleveland, Ohio, U.S.A.; thermoplastic elastic polyamides, including polyether block amides available from ATOFINA Chemicals, Inc. in Philadelphia, Pa., U.S.A., under the trade name PEBAX® polyether block amide; thermoplastic elastic polyesters, including those available from E.I. Du Pont de Nemours Company, under the trade name HYTREL®, and ARNITEL® from DSM Engineering Plastics of Evansville, Ind., U.S.A., and single-site or metallocene-catalyzed polyolefins having a density of less than about 0.89 grams/cubic centimeter such as metallocene polyethylene resins, available from Dow Chemical Company in Midland, Mich., U.S.A. under the trade name AFFINITY™; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are the rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight and having the same ratio of A blocks to B blocks. Diblocks with a different ratio of A to B blocks or a molecular weight larger or greater than one-half of triblock copolymers may be suitable for improving the foam polymer formula for producing low-density, soft, flexible, absorbent foam via polymer extrusion.

Suitably, the foam polymer formula includes up to about 90%, by weight, of polystyrene, and at least 10%, by weight, of thermoplastic elastomer. More particularly, the foam polymer formula may include between about 45% and about 90%, by weight, of polystyrene, and between about 10% and about 55%, by weight, of thermoplastic elastomer. Alternatively, the foam polymer formula may include between about 50% and about 80%, by weight, of polystyrene, and between about 20% and about 50%, by weight, of thermoplastic elastomer. For example, the foam polymer formula may include equal amounts of polystyrene and thermoplastic elastomer.

The foam polymer formula may include about 40% to about 80% by weight polystyrene and about 20% to about 60% by weight thermoplastic elastomer. The foam polymer formula may include about 50% to about 70% by weight polystyrene and about 30% to about 50% by weight thermoplastic elastomer.

A plasticizing agent can be included in the foam polymer formula. A plasticizing agent is a chemical agent that imparts flexibility, stretchability and workability. The type of plasticizing agent has an influence on foam gel properties, blowing agent migration resistance, cellular structure, including the fine cell size, and number of open-cells. Typically plasticizing agents are of low molecular weight. The increase in polymer chain mobility and free volume caused by incorporation of a plasticizing agent typically results in a Tg decrease, and plasticizing agent effectiveness is often characterized by this measurement. Petroleum-based oils, fatty acids, and esters are commonly used and act as external plasticizing agents or solvents because they do not chemically bond to the polymer yet remain intact in the polymer matrix upon crystallization.

The plasticizing agent increases cell connectivity by thinning membranes between cells to the point of creating porous connections between cells; thus, the plasticizing agent increases open-cell content. Suitably, the plasticizing agent is included in an amount between about 0.5% and about 10%, or between about 1% and about 10%, by weight, of the foam polymer formula. The plasticizing agent is gradually and carefully metered in increasing concentration into the foam polymer formula during the foaming process because too much plasticizing agent added at once creates cellular instability, resulting in cellular collapse.

Examples of suitable plasticizing agents include polyethylene, ethylene vinyl acetate, mineral oil, palm oil, waxes, esters based on alcohols and organic acids, naphthalene oil, paraffin oil, and combinations thereof. A commercially available example of a suitable plasticizing agent is a small-chain polyethylene that is produced as a catalytic polymerization of ethylene; because of its low molecular weight it is often referred to as a "wax." This low-density, highly branched polyethylene "wax" is available from Eastman Chemical Company of Kingsport, Tenn., U.S.A., under the trade designation EPOLENE® C-10.

In order for the foam to be used in personal care and medical product applications and many absorbent wiping articles and non-personal care articles, the foam must meet stringent chemical and safety guidelines. A number of plasticizing agents are FDA-approved for use in packaging materials. These plasticizing agents include: acetyl tributyl citrate; acetyl triethyl citrate; p-tert-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate); triethyl citrate; and 3-(2-xenyl)-1,2-epoxypropane.

The same material used as the thermoplastic elastomer may also be used as the plasticizing agent. For example, the KRATON® polymers, described above, may be used as a thermoplastic elastomer and/or a plasticizing agent. In which case, the foam polymer formula may include between about 10% and about 50%, by weight, of a single composition that acts as both a thermoplastic elastomer and a plasticizing agent. Described in an alternative manner, the foam may be formed without a plasticizing agent per se; in which case, the foam polymer formula may include between about 10% and about 50%, by weight, of the thermoplastic elastomer.

Foaming of soft, flexible polymers, such as thermoplastic elastomers, to a low density is difficult to achieve. The addition of a plasticizing agent makes foaming to low densities even more difficult to achieve. The method of the invention overcomes this difficulty through the inclusion of a surfactant in the foam polymer formula. The surfactant stabilizes the cells, thereby counteracting cellular collapse while retaining an open-cell structure. This stabilization of the cells creates cell uniformity and control of cell structure. In addition to enabling foaming of plasticized thermoplastic elastomer polymer containing foam formulations to low densities, the surfactant also provides wettability to enable the resulting foam to absorb fluid.

The foam pieces may be made from a thermoplastic absorbent foam such as a polyurethane foam. The thermoplastic foam may comprise surfactant and plasticizing agent. Polyurethane polymers are generally formed by the reaction of at least one polyisocyanate component and at least one polyol component. The polyisocyanate component may comprise one or more polyisocyanates. The polyol component may comprise one or more polyols. The concentration of a polyol may be expressed with regard to the total polyol component. The concentration of polyol or polyisocyanate may alternatively be expressed with regard to the total polyurethane concentration. Various aliphatic and aromatic polyisocyanates have been described in the art. The polyisocyanate utilized for forming the polyurethane foam typically has a functionality between from 2 and 3. The functionality may be no greater than about 2.5.

The foam may be prepared from at least one aromatic polyisocyanate. Examples of aromatic polyisocyanates include those having a single aromatic ring such as are toluene 2,4 and 2,6-diisocyanate (TDI) and naphthylene 1,5-diisocyanate; as well as those having at least two aromatic rings such as diphenylmethane 4,4'-, 2,4'- and 2,2'-diisocyanate (MDI).

The foam may be prepared from one or more (e.g. aromatic) polymeric polyisocyanates. Polymeric polyisocyanates typically have a (weight average) molecular weight greater than a monomeric polyisocyanate (lacking repeating units), yet lower than a polyurethane prepolymer. Thus, the polyurethane foam is derived from at least one polymeric polyisocyanate that lacks urethane linkages. In other words, the polyurethane foam is derived from a polymeric isocyanate that is not a polyurethane prepolymer. Polymeric polyisocyanates comprises other linking groups between repeat units, such as isocyanurate groups, biuret groups, carbodiimide groups, uretonimine groups, uretdione groups, etc. as known in the art.

Some polymeric polyisocyanates may be referred to as "modified monomeric isocyanate". For example pure 4,4'-methylene diphenyl diisocyanate (MDI) is a solid having a melting point of 38° C. and an equivalent weight of 125 g/equivalent. However, modified MDIs, are liquid at 38° C. and have a higher equivalent weight (e.g. 143 g/equivalent). The difference in melting point and equivalent weight is believed to be a result of a small degree of polymerization, such as by the inclusion of linking groups, as described above.

Polymeric polyisocyanates, including modified monomeric isocyanate, may comprise a mixture of monomer in combination with polymeric species inclusive of oligomeric species. For example, polymeric MDI is reported to contain 25-80% monomeric 4,4'-methylene diphenyl diisocyanate as well as oligomers containing 3-6 rings and other minor isomers, such as 2,2' isomer.

Polymeric polyisocyanates typically have a low viscosity as compared to prepolymers. The polymeric isocyanates utilized herein typically have a viscosity no greater than about 300 cps at 25° C. and in some embodiments no greater than 200 cps or 100 cps at 25° C. The viscosity is typically at least about 10, 15, 20 or 25 cps at 25° C.

The equivalent weight of polymeric polyisocyanates is also typically lower than that of prepolymers. The polymeric isocyanates utilized herein typically have an equivalent weight of no greater than about 250 g/equivalent and in some embodiments no greater than 200 g/equivalent or 175 g/equivalent. In some embodiments, the equivalent weight is at least 130 g/equivalent.

The average molecular weight (Mw) of polymeric polyisocyanates is also typically lower than that of polyurethane prepolymers. The polymeric isocyanates utilized herein typically have an average molecular weight (Mw) of no greater than about 500 Da and in some embodiments no greater than 450, 400, or 350 Da. The polyurethane may be derived from a single polymeric isocyanate or a blend of polymeric isocyanates. Thus, 100% of the isocyanate component is polymeric isocyanate(s). A major portion of the isocyanate component may be a single polymeric isocyanate or a blend of polymeric isocyanates. In these embodiments, at least 50, 60, 70, 75, 80, 85 or 90 wt-% of the isocyanate component is polymeric isocyanate(s).

Some illustrative polyisocyanates include for example, polymeric MDI diisocyanate from Huntsman Chemical Company, The Woodlands, Tex, under the trade designation "RUBINATE 1245"; and modified MDI isocyanate available from Huntsman Chemical Company under the trade designation "SUPRASEC 9561".

The aforementioned isocyanates are reacted with a polyol to prepare the polyurethane foam material. The polyurethane foams are hydrophilic, such that the foam absorbs aqueous liquids, particularly body fluids. The hydrophilicity of the polyurethane foams is typically provided by use of an isocyanate-reactive component, such as a polyether polyol, having a high ethylene oxide content.

Examples of useful polyols include adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide). Polyols having a high ethylene oxide content can also be made by other techniques as known in the art. Suitable polyols typically have a molecular weight (Mw) of 100 to 5,000 Da and contain an average functionality of 2 to 3.

The polyurethane foam is typically derived from (or in other words is the reaction product of) at least one polyether polyol having ethylene oxide (e.g. repeat) units. The polyether polyol typically has an ethylene oxide content of at least 10, 15, 20 or 25 wt-% and typically no greater than 75 wt-%. Such polyether polyol has a higher functionality than the polyisocyanate. The average functionality may be about 3. The polyether polyol typically has a viscosity of no greater than 1000 cps at 25° C. and in some embodiments no greater than 900, 800, or 700 cps. The molecular weight of the polyether polyol is typically at least 500 or 1000 Da and in some embodiments no greater than 4000 or 3500, or 3000 Da. Such polyether polyol typically has a hydroxyl number of at least 125, 130, or 140. An illustrative polyol includes for example a polyether polyol product obtained from the Carpenter Company, Richmond, Va. under the designation "CDB-33142 POLYETHER POLYOL", "CARPOL GP-5171".

One or more polyether polyols having a high ethylene oxide content and a molecular weight (Mw) of no greater than 5500, or 5000, or 4500, or 4000, or 3500, or 3000 Da, as just described, may be the primary or sole polyether polyols of the polyurethane foam. For example, such polyether polyols constitute at least 50, 60, 70, 80, 90, 95 or 100 wt-% of the total polyol component. Thus, the polyurethane foam may comprise at least 25, 30, 35, 40, 45 or 50 wt-% of polymerized units derived from such polyether polyols.

One or more polyether polyols having a high ethylene oxide content may be utilized in combination with other polyols. The other polyols may constitute at least 1, 2, 3, 4, or 5 wt-% of the total polyol component. The concentration of such other polyols typically does not exceed 40, or 35, or 30, or 25, or 20, or 15, or 10 wt-% of the total polyol component, i.e. does not exceed 20 wt-%, or 17.5 wt-%, or 15 wt-%, or 12.5 wt-%, or 10 wt-%, or 7.5 wt-%, or 5 wt-% of the polyurethane. Illustrative other polyols include a polyether polyol product (Chemical Abstracts Number 25791-96-2) that can be obtained from the Carpenter Company, Richmond, Va. under the designation "CARPOL GP-700 POLYETHER POLYOL" and a polyether polyol product (Chemical Abstracts Number 9082-00-2) that can be obtained from Bayer Material Science, Pittsburgh, Va. under the trade designation "ARCOL E-434". Such optional other polyols may comprise polypropylene (e.g. repeat) units.

The polyurethane foam generally has an ethylene oxide content of at least 10, 11, or 12 wt-% and no greater than 20, 19, or 18 wt-%. The polyurethane foam may have an ethylene oxide content of no greater than 17 or 16 wt-%.

The kinds and amounts of polyisocyanate and polyol components are selected such that the polyurethane foam is relatively soft, yet resilient. These properties can be characterized for example by indentation force deflection and constant deflection compression set, as measured according to the test methods described in the examples. The polyurethane foam may have an indentation force deflection of less than 75N at 50%. The indentation force deflection at 50% may be less than 70N, or 65N, or 60 N. The polyurethane foam may have an indentation force deflection of less than 100N at 65%. The indentation force deflection at 65% may be less than 90N, or 80N, or 70 N, or 65N, or 60N. The indentation force deflection at 50% or 65% may be typically at least 30N or 35N. The constant deflection compression set at 50% deflection can be zero and is typically at least 0.5, 1 or 2% and generally no greater than 35%. The constant deflection compression set at 50% deflection may be no greater than 30%, or 25%, or 20%, or 15%, or 10%.

The polyurethane foam may comprise known and customary polyurethane formation catalysts such as organic tin compounds and/or an amine-type catalyst. The catalysts may beused in an amount of from 0.01 to 5 wt-% of the polyurethane. The amine-type catalyst is typically a tertiary amine Examples of suitable tertiary amine include monoamines such as triethylamine, and dimethyl cyclohexylamine; diamines such as tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,5-diazabicyclo(5,4,0)undecene-7 (DBU), and 1,5-diazabicyclo(4,3,0)nonene-5; and organic acid salts of the diazabicycloalkenes such as phenol salt, 2-ethylhexanoate and formate of DBU. These amines can be used either singly or in combination. The amine-type catalyst can be used in an amount no greater than 4, 3, 2, 1 or 0.5 wt-% of the polyurethane.

The polyurethane typically comprises a surfactant to stabilize the foam. Various surfactants have been described in the art. A silicone surfactant may be employed that comprises ethylene oxide (e.g. repeat) units, optionally in combination with propylene oxide (e.g. repeat) units such as commercially available from Air Products under the trade designation "DABCO DC-198". The concentration of hydrophilic surfactant may typically range from about 0.05 to 1 or 2 wt-% of the polyurethane.

The polyurethane foam may comprise various additives such as surface active substances, foam stabilizers, cell regulators, blocking agents to delay catalytic reactions, fire retardants, chain extenders, crosslinking agents, external and internal mold release agents, fillers, pigments (titanium dioxide), colorants, optical brighteners, antioxidants, stabilizers, hydrolysis inhibitors, as well as anti-fungal and anti-bacteria substances. Such other additives are typically collectively utilized at concentrations ranging from 0.05 to 10 wt-% of the polyurethane.

The absorbent foam may be white in color. Certain hindered amine stabilizers can contribute to discoloration, such as yellowing, of the absorbent foam. The absorbent foam may be free of diphenylamine stabilizer and/or phenothiazine stabilizer.

The absorbent foam may be a colored (i.e. a color other than white). The white or colored absorbent foam can include a pigment in at least one of the components. Pigment may be combined with a polyol carrier and is added to the polyol liquid stream during manufacture of the polyurethane foam. Commercially available pigments include for example DispersiTech™ 2226 White, DispersiTech™ 2401 Violet, DispersiTech™ 2425 Blue, DispersiTech™ 2660 Yellow, and DispersiTech™ 28000 Red from Milliken in Spartansburg, S.C. and Pdi® 34-68020 Orange from Ferro in Cleveland, Ohio.

In the production of polyurethane foams, the polyisocyanate component and polyol component are reacted such that an equivalence ratio of isocyanate groups to the sum of hydroxyl groups is no greater than 1 to 1. The components may be reacted such that there are excess hydroxyl groups (e.g. excess polyol). The equivalence ratio of isocyanate groups to the sum of the hydroxy groups may be at least 0.7 to 1. For example, the ratio may be at least 0.75:1, or at least 0.8:1.

The hydrophilic (e.g. polyol(s)) component(s) of the (e.g. polyurethane) polymeric foam provide the desired absorption capacity of the foam. Thus the foam may be free of superabsorbent polymer. Further, the polyurethane foam is free of amine or imine complexing agent such as ethylenimine, polyethylenimine, polyvinylamine, carboxy-methylated polyethylenimines, phosphono-methylated polyethylenimines, quaternized polyethylenimines and/or dithiocarbamitized polyethylenimines; as described for example in U.S. Pat. Nos. 6,852,905 and 6,855,739.

The polymeric (e.g. polyurethane) foam typically has an average basis weight of at least 100, 150, 200, or 250 gsm and typically no greater than 500 gsm. The average basis weight may be no greater than 450, or 400 gsm. The average density of the (e.g. polyurethane) polymeric foam is typically at least 3, 3.5 or 4 lbs/ft3 and no greater than 7 lbs/ft3.

The open-celled foam is a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. The aqueous phase to oil phase ratio may be between about 10:1 and about 75:1, and the aqueous phase to oil phase ratio may be between about 13:1 and about 65:1. This is termed the "water-to-oil" or W:O ratio and can be used to determine the density of the resulting polyHIPE foam. As discussed, the oil phase may contain one or more of monomers, comonomers, photoinitiators, crosslinkers, and emulsifiers, as well as optional components. The water phase may contain water and one or more components such as electrolyte, initiator, or optional components.

The open-cell foam can be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, or after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE can then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion can be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. Foam pieces may be squeezed free of most of the aqueous phase by using compression, for example by running the heterogeneous mass comprising the foam pieces through one or more pairs of nip rollers. The nip rollers can be positioned such that they squeeze the aqueous phase out of the foam pieces. The nip rollers can be porous and have a vacuum applied from the inside such that they assist in drawing aqueous phase out of the foam pieces. Nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller can be pressurized while the other, for example the second nip roller, can be evacuated, so as to both blow and draw the aqueous phase out the of the foam. The nip rollers may also be heated to assist in removing the aqueous phase. Nip rollers may be applied to non-rigid foams, that is, foams whose walls would not be destroyed by compressing the foam pieces.

In place of or in combination with nip rollers, the aqueous phase may be removed by sending the foam pieces through a drying zone where it is heated, exposed to a vacuum, or a combination of heat and vacuum exposure. Heat can be applied, for example, by running the foam though a forced air oven, IR oven, microwave oven or radiowave oven. The extent to which a foam is dried depends on the application. Greater than 50% of the aqueous phase may be removed. Greater than 90%, and in still other embodiments greater than 95% of the aqueous phase may be removed during the drying process.

Open-cell foam may be produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams.

"Toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type can have styrene and vinyl chloride.

The oil phase may further contain an emulsifier used for stabilizing the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched C16-C24 alcohols, linear unsaturated C16-C22 alcohols, and linear saturated C12-C14 alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they can have between about 1% and about 20%, in certain embodiments from about 2% to about 15%, and in certain other embodiments from about 3% to about 12% by weight of the oil phase. Coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. Ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, a-hydroxyalkyl phenones, a-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); a-,a-dimethoxy-a-hydroxy acetophenone (sold by Ciba Speciality Chemicals as DAROCUR® 1173); 2-methyl-1-[4-(methyl thio)phenyl]-2-morpholino-propan-1-one (sold by Ciba Speciality Chemicals as IRGACURE® 907); 1-hydroxycyclohexylphenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl)phenyl]propanone] (sold by Lambeth spa, Gallarate, Italy as ESACURE® KIP EM.

The dispersed aqueous phase of a HIPE can have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. The initiator may be present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. To reduce the potential for premature polymerization which may clog the emulsification system, addition of the initiator to the monomer phase may be just after or near the end of emulsification.

Photoinitiators present in the aqueous phase may be at least partially water soluble and can have between about 0.05% and about 10%, and in certain embodiments between about 0.2% and about 10% by weight of the aqueous phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane] disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis (2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination. The enrobeable elements may be hydrophobic or hydrophilic. The enrobeable elements may be treated to be made hydrophobic. The enrobeable elements may be treated to become hydrophilic.

The constituent fibers of the heterogeneous mass can be comprised of polymers such as polyethylene, polypropylene, polyester, and blends thereof. The fibers can be spunbound fibers. The fibers can be meltblown fibers. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers can range from about 0.1 denier to about 100 denier.

In one aspect, known absorbent web materials in an as-made can be considered as being homogeneous throughout. Being homogeneous, the fluid handling properties of the absorbent web material are not location dependent, but are substantially uniform at any area of the web. Homogeneity can be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability can be accomplished without a decrease in capillarity.

The heterogeneous mass may also include superabsorbent material that imbibe fluids and form hydrogels. These materials are typically capable of absorbing large quantities of body fluids and retaining them under moderate pressures. The heterogeneous mass can include such materials dispersed in a suitable carrier such as cellulose fibers in the form of fluff or stiffened fibers. The heterogeneous mass may include thermoplastic particulates or fibers. The materials, and in particular thermoplastic fibers, can be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). The polymer comprising the sheath often melts at a different, typically lower, temperature than the polymer comprising the core. As a result, these bicomponent fibers provide hydrothermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

The length of bicomponent fibers can vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine can have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective thermally bonded fibrous matrix.

The heterogeneous mass can also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, such as, for example from about 0.9 to about 1.5 cm. Suitable nonbonding thermoplastic fibers can have a decitex in the range of about 1.5 to about 35 decitex, such as, for example, from about 14 to about 20 decitex. However structured, the total absorbent capacity of the heterogeneous mass containing foam pieces should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins. The heterogeneous mass can also include other optional components sometimes used in absorbent webs. For example, a reinforcing scrim can be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; disposable diapers; incontinence articles, for example pads, adult diapers; homecare articles, for example wipes, pads, towels; and beauty care articles, for example pads, wipes, and skin care articles, such as used for pore cleaning.

The heterogeneous mass may be used as an absorbent core for an absorbent article. The absorbent core may be relatively thin, less than about 5 mm in thickness, or less than about 3 mm, or less than about 1 mm in thickness. Cores having a thickness of greater than 5 mm are also contemplated herein. Thickness can be determined by measuring the thickness at the midpoint along the longitudinal centerline of the absorbent structure by any means known in the art for doing while under a uniform pressure of 0.25 psi. The absorbent core can comprise absorbent gelling materials (AGM), including AGM fibers, as is known in the art.

The heterogeneous mass may be formed or cut to a shape, the outer edges of which define a periphery. Additionally, the heterogeneous mass may be continuous such that it may be rolled or wound upon itself, with or without the inclusion of preformed cut lines demarcating the heterogeneous mass into preformed sections. When used as an absorbent core, the shape of the heterogeneous mass can be generally rectangular, circular, oval, elliptical, or the like. Absorbent core can be generally centered with respect to the longitudinal centerline and transverse centerline of an absorbent article. The profile of absorbent core can be such that more absorbent is disposed near the center of the absorbent article. For example, the absorbent core can be thicker in the middle, and tapered at the edges in a variety of ways known in the art.

Applicants have found that the absorbent structure may exhibit increasing compressive energy through a usage cycle. The heterogeneous mass exhibits a compressive energy (measured in millijoules (mJ)) when wet representing between 100% and up to 200% of the dry compressive energy, such as, for example, between 100% and 180%, between 110% and 170%, between 120% and 160%, between 125% and 150%, or between 130% and 150%. This surprising result allows one to create a product that is near garment-like when dry that changes during use such that the article increases in compressive energy when wet.

The dry compressive energy is between 10% and 99% of the wet compressive energy measurement such as, for example, between 15% and 80%, between 20% and 75%, between 25% and 70%, such as, for example, 30%, 35%, 40%, 45%, 50%, 60%, or 65% of the wet compressive energy measurement. The wet compressive energy is calculated when the sample is loaded with 7 ml of 10% saline solution.

Recovery energy is an indicator of how well a core/product can retain or regain is original shape to offer a larger area of coverage to the product-to-body interface—more specifically the amount of work the core/product will perform against the consumer's body and garment. The upper limit for recovery energy should be the $1_{st}$ Cycle Compressive Energy in the dry state. The fifth cycle recovery energy, as measured by the bunched compression test, may be used as measure of the product when it is in use. Testing it in a dry state and a wet state allows one to see how the absorbent structure reacts while being used before and after fluid is absorbed by the product.

Without being bound by theory, Applicants have found that compressive & recovery energies, peak force, and core/product caliper are all important components that exhibit how an absorbent product will fit, feel and protect—each components of this ratio will be discussed to explain its role in regards to delivering these benefits.

As previously stated, the peak force is an indicator of the flexibility of the absorbent structure. Without being bound by theory, Applicants have found that a lower peak force allows an absorbent product to be more "garment like". When balanced with the appropriate fifth cycle Recovery Energy range according to the bunched compression test, a product may be "garment like" and still capable of retaining its shape during use without creating bunching or comfort issues for the consumer. The $1^{st}$ cycle compressive energy, as measured by the bunched compression test, is a measure of the effort required to "break-in" the product—for it to more naturally conform and fit to her body. The upper limit for recovery energy should be the $1^{st}$ Cycle Compressive Energy in the dry state—it is preferred that this energy approaches the upper

| Sample | | RE 5th Cycle (mJ) | PF 1st Cycle (Grams) | CALIPER mm | PERCENT DIFF CALIPER |
|---|---|---|---|---|---|
| Invention A | DRY | 1.5 | 69.88 | 1.79 | 23% |
| Invention A | WET | 2.11 | 82.96 | 2.2 | |
| Invention B | DRY | 0.98 | 56.68 | 3.77 | 3% |
| Invention B | WET | 0.64 | 65.99 | 3.9 | |
| Invention C | DRY | 1.39 | 77.59 | 3.29 | 13% |
| Invention C | WET | 1.01 | 98.36 | 3.72 | |
| Invention D | DRY | 0.78 | 45.14 | 1.39 | 149% |
| Invention D | WET | 1.01 | 83.26 | 3.44 | |
| Prior Art E | DRY | 0.07 | 19.84 | 1.69 | 202% |
| Prior Art E | WET | 1.12 | 61.43 | 5.11 | |
| Prior Art F | DRY | 2.88 | 177.85 | 1.24 | 44% |
| Prior Art F | WET | 0.62 | 105.69 | 1.78 | |
| Prior Art G | DRY | 3.58 | 170.15 | 2.29 | 18% |
| Prior Art G | WET | 2.86 | 156.86 | 2.7 | | compressive energy limit without sacrificing the resultant comfort of the core/product.

The table above lists several examples of inventions that exhibit the desired properties (Invention A-Invention D). Invention A-C represent examples of a heterogeneous mass enrobed by open cell foam. Inventions B-C have undergone additional solid state formation. Invention D represents an improved core system using AGM. Prior Art E-G represent currently available absorbent structures in the market including a traditional HIPE core layer structure (Prior Art G).

Applicants have found that the desired product are able to exhibit the desired properties in 15 use while having a caliper change of less than 200% combined with a 1st cycle dry peak force (PF) of between 30 and 150 grams, and a 5th cycle dry recovery energy of between 0.1 mJ and 2.8 mJ. The caliper change may be between 1% and 200%, between 10% and 100%, or between 20% and 80%. The absorbent structures may exhibit a fifth cycle recovery energy for a dry cycle that is between 0.1 mJ and 2.8 mJ, such as, for example, 0.2 mJ and 2.5 mJ, 0.5 mJ and 2.0 mJ, 20 or 0.9 mJ and 1.5 mJ. Applicants have found that having a fifth dry cycle recovery energy between 0.1 mJ and 2.8 mJ represents improved recovery during use allowing products to maintain sufficient structure while still being flexible and garment like. Applicants have found that absorbent structures that exhibit a first cycle peak force for a dry cycle that is between 30 and 150 grams have sufficient flexibility and the minimum necessary level of structure. The absorbent structures may exhibit a first cycle peak force for a dry cycle that is between 30 and 150 grams, such as, for example, between 40 and 120 grams, between 45 and 100 grams, or between 50 and 80 grams. Core caliper is a highly consumer relevant indicator of how garment or panty-like an absorbent article will be when worn due to its connection to flexibility and bulk. A core/product with less caliper occupies less space at the panty-to-body interface and is more flexible i.e. can more freely move as the panty would naturally.

As shown in Table 1(Invention examples B-C), one can affect the material through the use of solid state formation, such as, for example, ring rolling. Formation means known for deforming a generally planar fibrous web into a three-dimensional structure are utilized in the present invention to modify as-made absorbent materials into absorbent materials having relatively higher permeability without a significant corresponding decrease in capillary pressure. Formation means may comprise a pair of inter-meshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. The pair of intermeshing rolls of the instant invention may be considered as equivalent to a roll and an inter-meshing element, wherein the inter-meshing element can be another roll, a cord, a plurality of cords, a belt, a pliable web, or straps. Likewise, other known formation technologies, such as creping, necking/consolidation, corrugating, embossing, button break, hot pin punching, and the like are believed to be able to produce absorbent materials having some degree of relatively higher permeability without a significant corresponding decrease in capillary pressure. Formation means utilizing rolls include "ring rolling", a "SELF" or "SELF'ing" process, in which SELF stands for Structural Elastic Like Film, as "micro-SELF", and "rotary knife aperturing" (RKA); as described in U.S. Pat. No. 7,935,207 Zhao et al., granted May 3, 2011. Other references related to formation means include U.S. Pat. No. 6,203,654 McFall et al., granted Mar. 20, 2001 and U.S. Pat. No. 6,410,820 McFall et al., granted Jun. 25, 2002. The heterogeneous mass exhibits an increasing compression energy during a usage cycle. The heterogeneous mass may exhibit a change in energy from a 1st cycle and a 20th cycle that is less than 50% of the initial energy of the 1st cycle. The heterogeneous mass exhibits a change in compression energy from dry to wet that is less than 20% of the initial dry energy.

As shown in the table above, the heterogeneous mass (Inventions A-C) exhibits a $5^{th}$ cycle Recovery Energy of between 0.9 mJ and 2 mJ, such as for example, 0.98, 1.1, 1.2, 1.3, 1.4, and 1.5 mJ.

The absorbent structure may serve as any portion of an absorbent article. The absorbent structure may serve as the absorbent core of an absorbent article. The absorbent structure may serve as a portion of the absorbent core of an absorbent article. More than one absorbent structure may be combined wherein each absorbent structure differs from at least one other absorbent structure in either the choice of enrobeable elements or by a characteristic of its open-cell foam pieces. The different two or more absorbent structures may be combined to form an absorbent core. The absorbent article may further comprise a topsheet and a backsheet.

The absorbent structure may be used as a topsheet for an absorbent article. The absorbent structure may be combined with an absorbent core or may only be combined with a backsheet.

The absorbent structure may be combined with any other type of absorbent layer such as, for example, a layer of cellulose, a layer comprising superabsorbent gelling materials, a layer of absorbent airlaid fibers, or a layer of absorbent foam. Other absorbent layers not listed are contemplated herein.

The absorbent structure may be utilized by itself for the absorption of fluids without placing it into an absorbent article.

An absorbent article may comprise a liquid pervious topsheet. The topsheet suitable for use herein can comprise wovens, non-wovens, and/or three-dimensional webs of a liquid impermeable polymeric film comprising liquid permeable apertures. The topsheet for use herein can be a single layer or may have a multiplicity of layers. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548. The absorbent articles of FIGS. 1 to 17 comprising embodiments of the absorbent structure can also comprise a backsheet and a topsheet. The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. The backsheet may also allow the transfer of at least water vapour, or both water vapour and air through it.

Especially when the absorbent article finds utility as a sanitary napkin or panty liner, the absorbent article can be also provided with a panty fastening means, which provides means to attach the article to an undergarment, for example a panty fastening adhesive on the garment facing surface of the backsheet. Wings or side flaps meant to fold around the crotch edge of an undergarment can be also provided on the side edges of the napkin.

FIG. 1 is a plan view of a sanitary napkin 10 comprising a topsheet 12, a backsheet (not shown), an absorbent core 16 located between the topsheet 12 and the backsheet, a longitudinal axis 24, and a transverse axis 26. The absorbent core 16 comprises of a heterogeneous mass 18 comprising elements 30 and one or more discrete foam pieces 20 that enrobe the at least one element 30 of the heterogeneous mass 18. As shown in FIG. 1 the elements 30 are fibers 22. A portion of the topsheet is cut out in order to show underlying portions.

Figure 2:
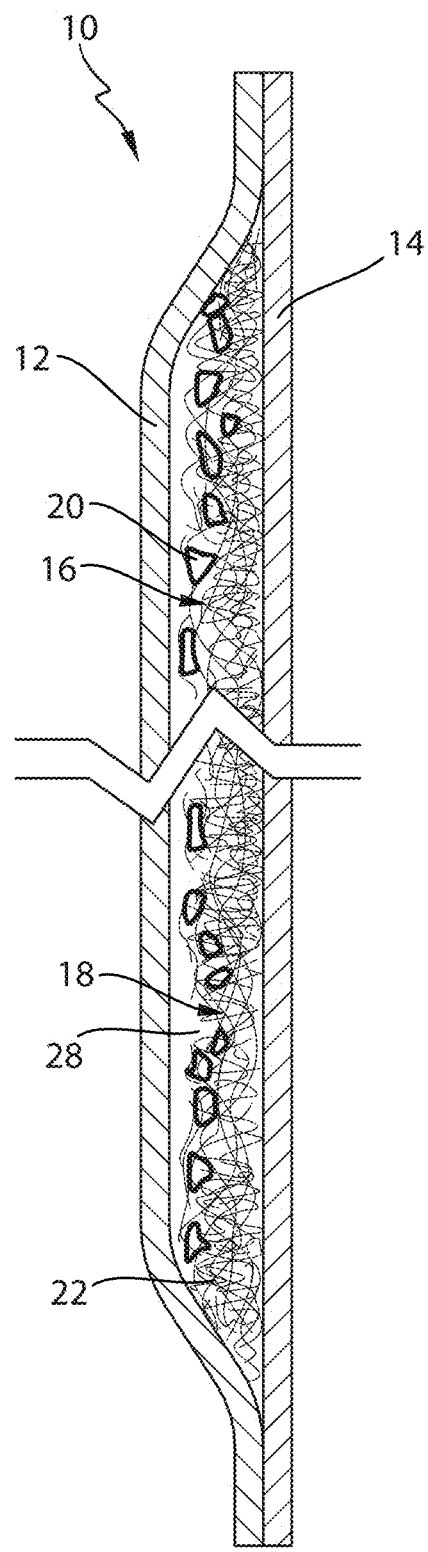
FIG. 2 is a cross section view of the absorbent article of FIG. 1 taken along line 2-2.
Figure 3:
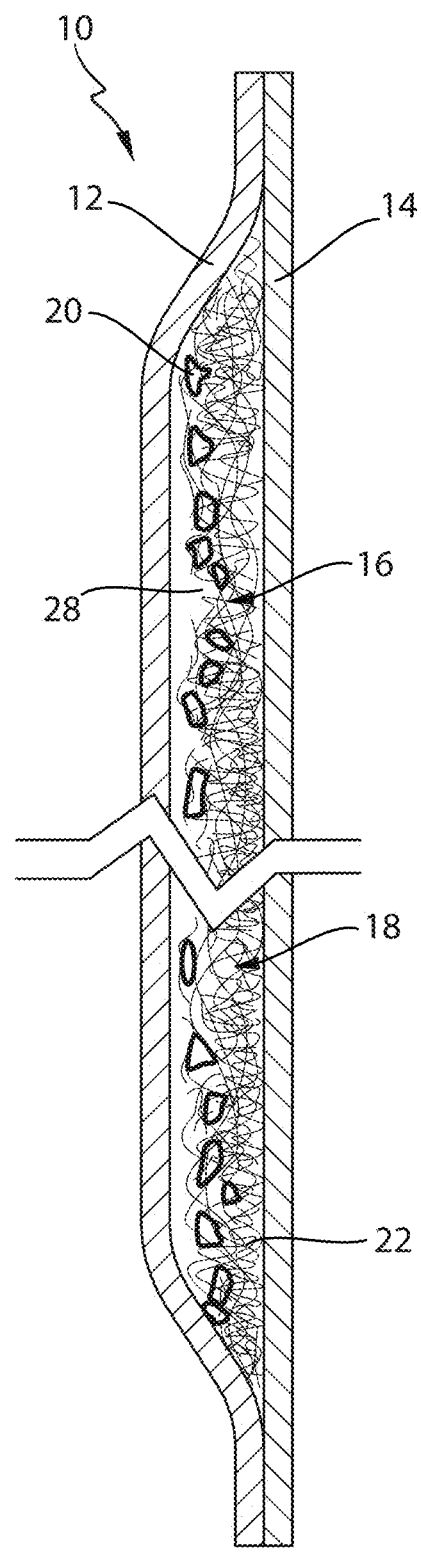
FIG. 3 is a cross section view of the absorbent article of FIG. 1 taken along line 3-3.

FIGS. 2 and 3 are cross sections of pad shown in FIG. 1, cut through the 2-2 vertical plane along the longitudinal axis 24 and cut through the 3-3 vertical plane along the transverse axis 26, respectively. As can be seen in FIGS. 2 and 3, the absorbent core 16 is between the topsheet 12 and the backsheet 14. As shown in the embodiment of FIGS. 2 and 3, the discrete foam pieces 20 are spread out throughout the absorbent core and enrobe the elements 30 of the heterogeneous mass 18. The discrete pieces 20 of foam may extend beyond the enrobeable elements to form part of the outer surface of the heterogeneous mass. Additionally, discrete pieces of foam may be fully intertwined within the heterogeneous mass of the absorbent core. Voids 28 containing gas are located between the fibers 22.

Figure 4:
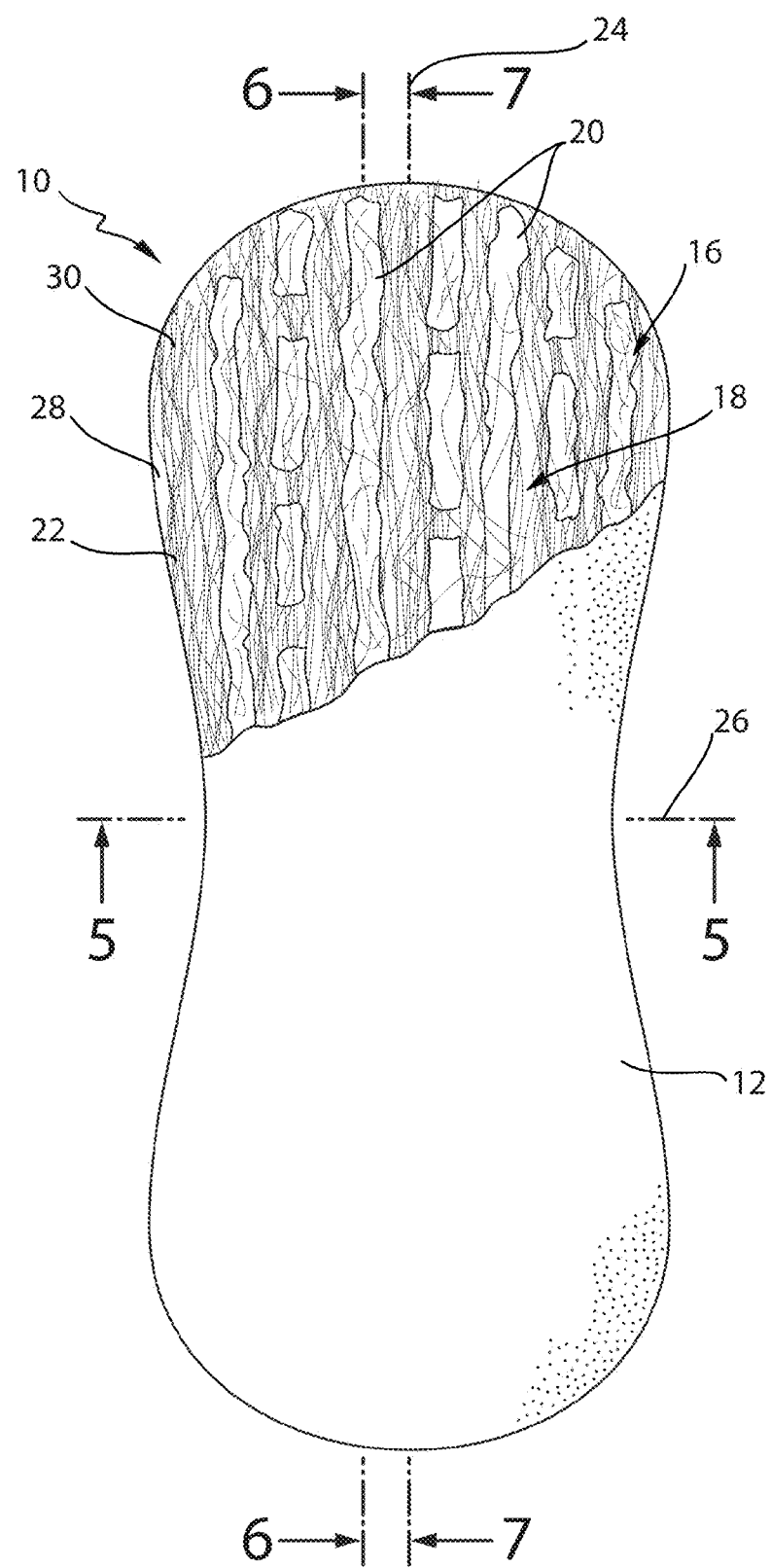
FIG. 4 is a top view of an absorbent article.

FIG. 4 is a plan view of a sanitary napkin 10 illustrating an embodiment of the invention. The sanitary napkin 10 comprises a topsheet 12, a backsheet (not shown), an absorbent core 16 located between the topsheet 12 and the backsheet, a longitudinal axis 24, and a transverse axis 26. The absorbent core 16 comprises of a heterogeneous mass 18 comprising elements 30 and one or more discrete foam pieces 20 that enrobe the at least one element 30 of the heterogeneous mass 18. As shown in FIG. 4, the elements 30 are fibers 22. A portion of the topsheet is cut out in order to show underlying portions. As shown in FIG. 4 the discrete foam pieces 20 may be continuous along an axis of the heterogeneous mass, such as, for example, the longitudinal axis. Further, the discrete foam 20 may be arranged to form a line in the heterogeneous mass. The discrete foam pieces 20 are shown proximate to the top of the heterogeneous mass 18 but may also be located at any vertical height of the heterogeneous mass 18 such that enrobeable elements 30 may be located above and below the one or more of the discrete foam pieces 20. FIGS. 5, 6 and 7 are cross sections of the pad shown in FIG. 4, cut through the 5-5, the 66, and the 7-7 vertical planes, respectively. The 5-5 vertical plane is parallel to the transverse axis of the pad and the 6-6 and 7-7 vertical planes are parallel to the longitudinal axis. As can be seen in FIGS. 5 to 7, the absorbent core 16 is between the topsheet 12 and the backsheet 14. As shown in the embodiment of FIG. 5, the discrete foam pieces 20 are spread out throughout the absorbent core and enrobe the elements 30 of the heterogeneous mass 18. As shown in FIG. 6, a discrete foam piece 20 may be continuous and extend along the heterogeneous mass. As shown in FIG. 7, the heterogeneous mass may not have any discrete foam pieces along a line cross section of the absorbent core. Voids 28 containing gas are located between the fibers 22.

Figure 8:
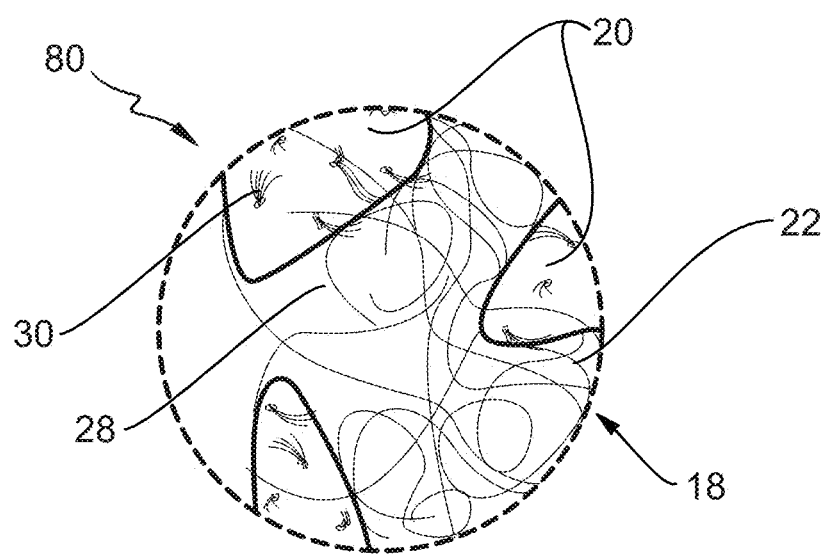
FIG. 8 is a magnified view of a portion of FIG. 5.

FIG. 8 is a zoomed in view of a portion of FIG. 5 indicated on FIG. 5 by a dotted line circle 80. As shown in FIG. 8, the heterogeneous mass 18 comprises discreet foam pieces 20 and enrobeable elements 30 in the form of fibers 22. Voids 28 containing gas are located between the fibers 22.

Figure 9:
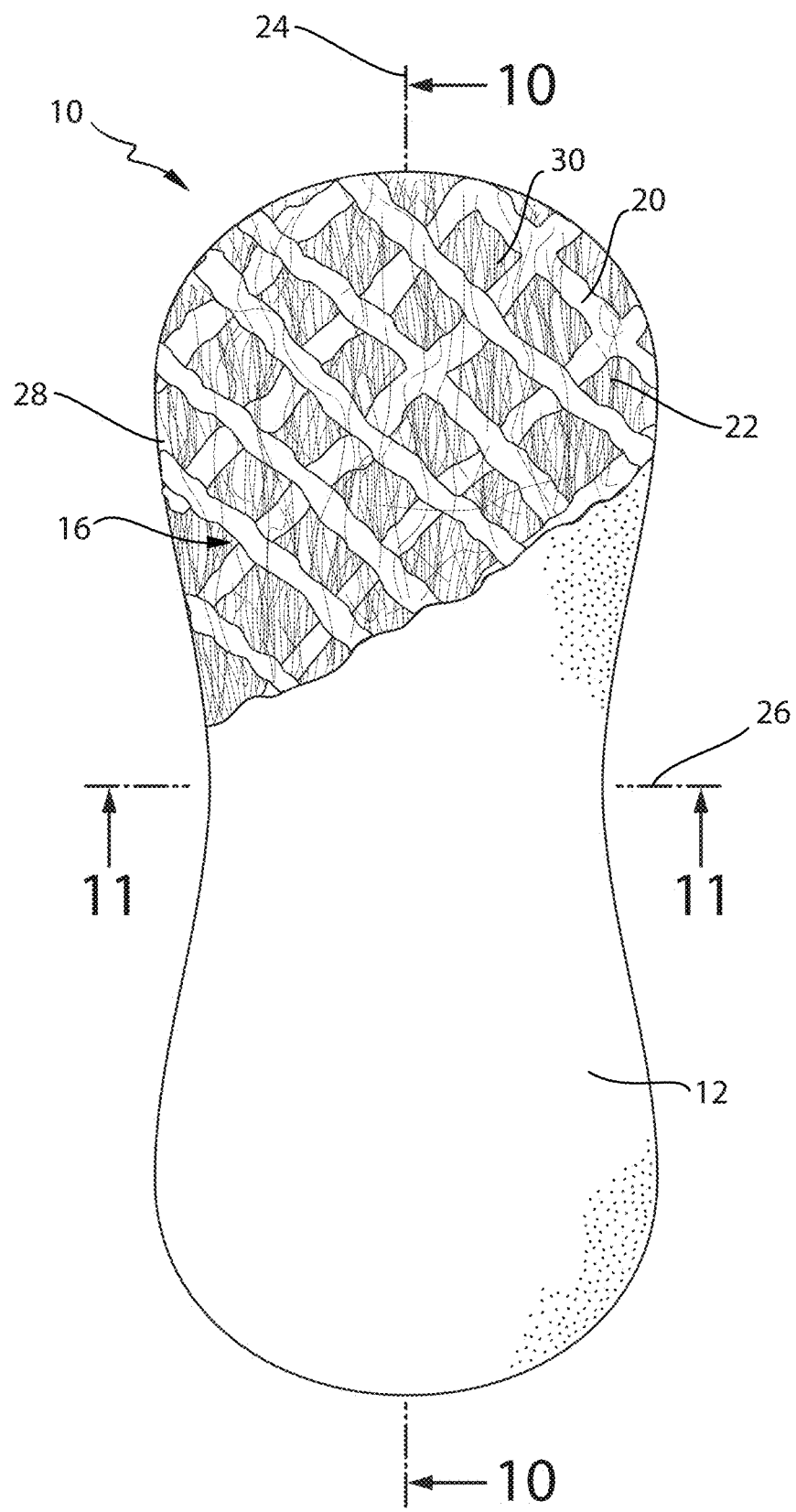
FIG. 9 is a top view of an absorbent article.

FIG. 9 is a plan view of a sanitary napkin 10 illustrating an embodiment of the invention. The sanitary napkin 10 comprises a topsheet 12, a backsheet (not shown), an absorbent core 16 located between the topsheet 12 and the backsheet, a longitudinal axis 24, and a transverse axis 26. The absorbent core 16 comprises of a heterogeneous mass 18 comprising elements 30 and one or more discrete foam pieces 20 that enrobe the at least one element 30 of the heterogeneous mass 18. As shown in FIG. 9, the elements 30 are fibers 22. A portion of the topsheet is cut out in order to show underlying portions. As shown in FIG. 9, the discrete foam pieces 20 may form a pattern, such as, for example, a checkerboard grid.

Figure 10:
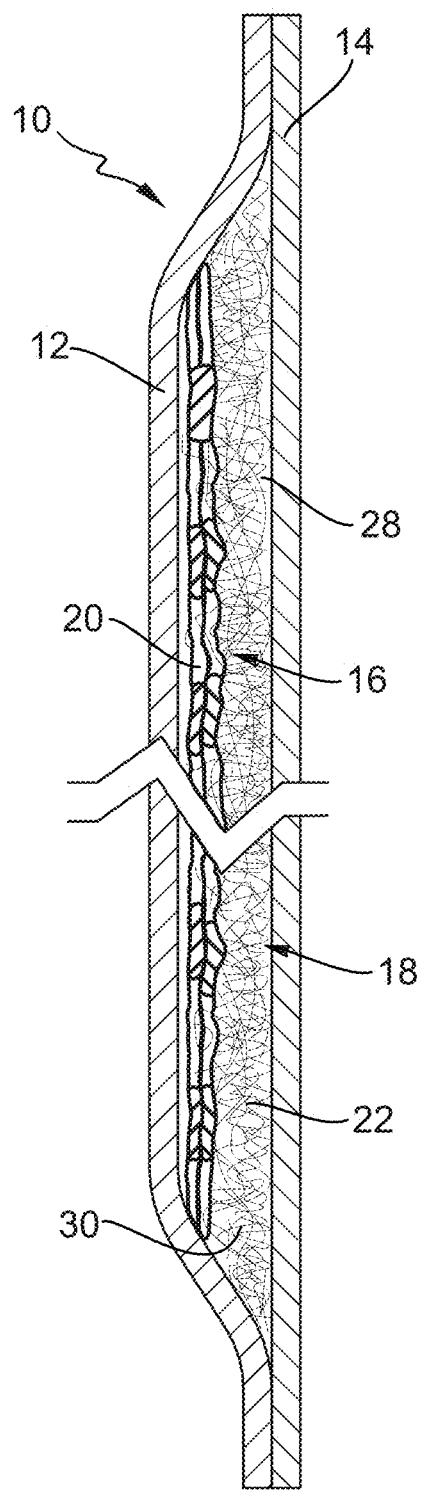
FIG. 10 is a cross section view of the absorbent article of FIG. 9 taken along line 10-10.
Figure 11:
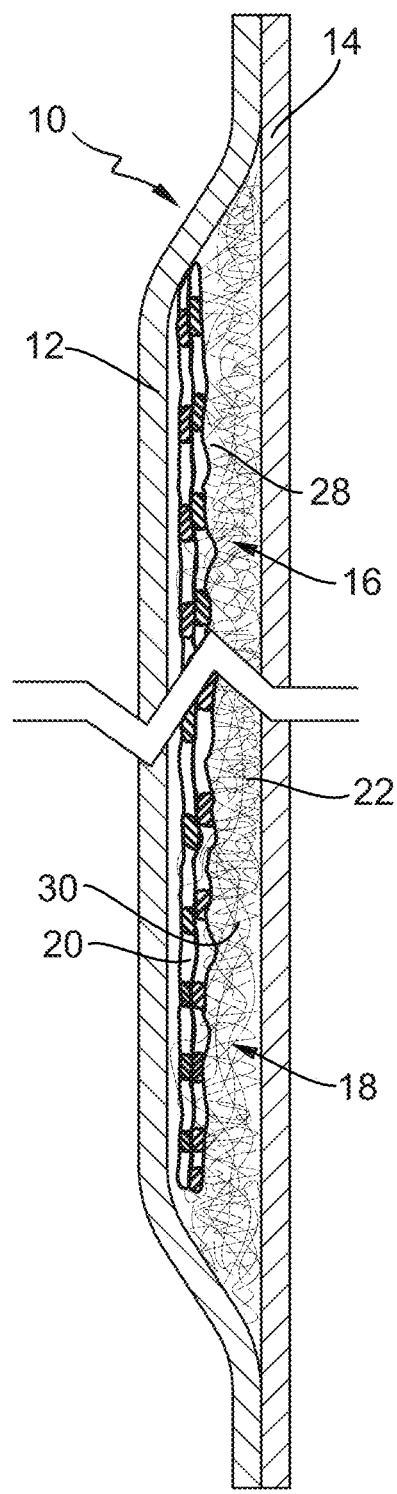
FIG. 11 is a cross section view of the absorbent article of FIG. 9 taken along line 11-11.
Figure 12:
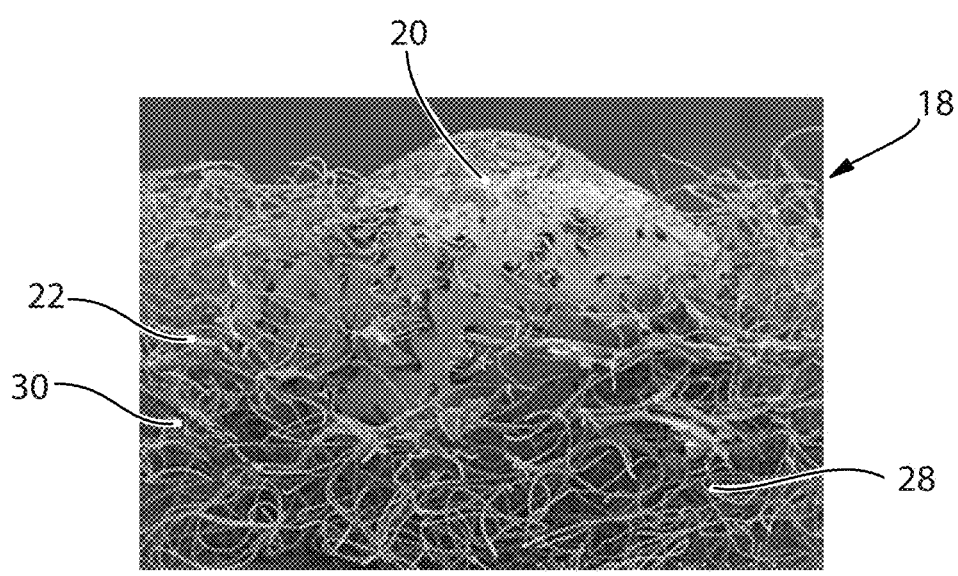
FIG. 12 is an SEM of a representative HIPE foam piece.

FIGS. 10 and 11 are cross sections of the pad shown in FIG. 9, cut through the 10-10 and 11-11 vertical planes, respectively. As can be seen in FIGS. 10 and 11, the absorbent core 16 is between the topsheet 12 and the backsheet 14. As shown in the embodiment of FIGS. 10 and 11, the discrete foam pieces 20 are spread out throughout the absorbent core and enrobe the elements 30 in the form of fibers 22 of the heterogeneous mass 18. Voids 28 containing gas are located between the fibers 22. FIGS. 12 to 16 are SEM micrographs of HIPE foam pieces 20 intertwined within a heterogeneous mass 18 comprising nonwoven fibers 22. FIG. 12 shows a SEM micrograph taken at 15× magnification. As shown in FIG. 12, a discrete HIPE foam piece 20 and the elements 30 in the form of fibers 22 are intertwined. The HIPE foam piece 20 enrobes one or more of the fibers 22 of the heterogeneous mass 18. The fibers 22 of the heterogeneous mass 18 cross through the HIPE foam piece 20. Voids 28 containing gas are located between fibers 22.

Figure 13:
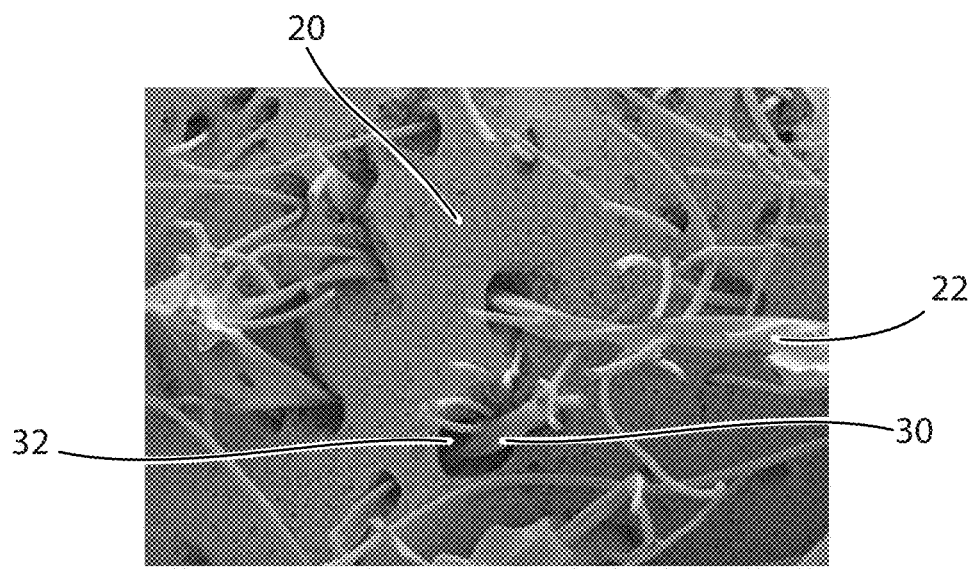
FIG. 13 is a magnified view of the SEM of FIG. 12.

FIG. 13 shows the absorbent core of FIG. 12 at a magnification of 50×. As shown in FIG. 13, the HIPE foam pieces 20 envelop a portion of one or more fibers 22 such that the fibers bisect through the HIPE foam pieces 20. The HIPE foam pieces 20 enrobe the fibers such that the pieces are not free to move about within the absorbent core. As shown in FIG. 13, vacuoles 32 may exist within the enrobing foam 20. Vacuoles 32 may contain a portion of the enrobeable element 30.

Figure 14:
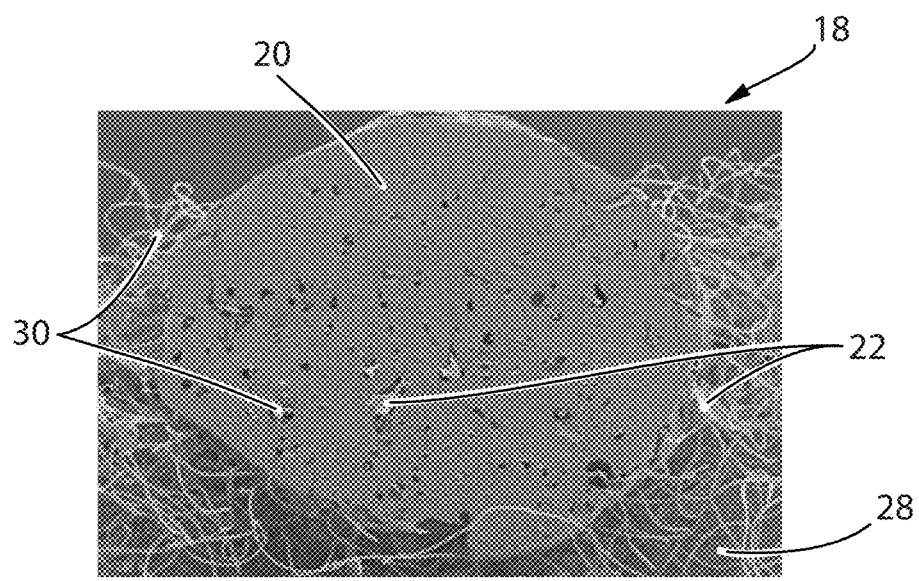
FIG. 14 is a cross section view of the SEM of FIG. 12.

FIG. 14 shows another SEM micrograph of a cross section of a discrete HIPE foam piece taken at 15× magnification. As shown in FIG. 14, the HIPE foam piece 20 may extend beyond the elements 30 of the heterogeneous mass 18 to form a portion of the outer surface of the heterogeneous mass 18. The HIPE foam pieces 20 enrobes one or more of the fibers 22 of the heterogeneous mass 18. The fibers of the absorbent core cross through the HIPE foam piece. Voids 28 containing gas are located between fibers 22.

Figure 15:
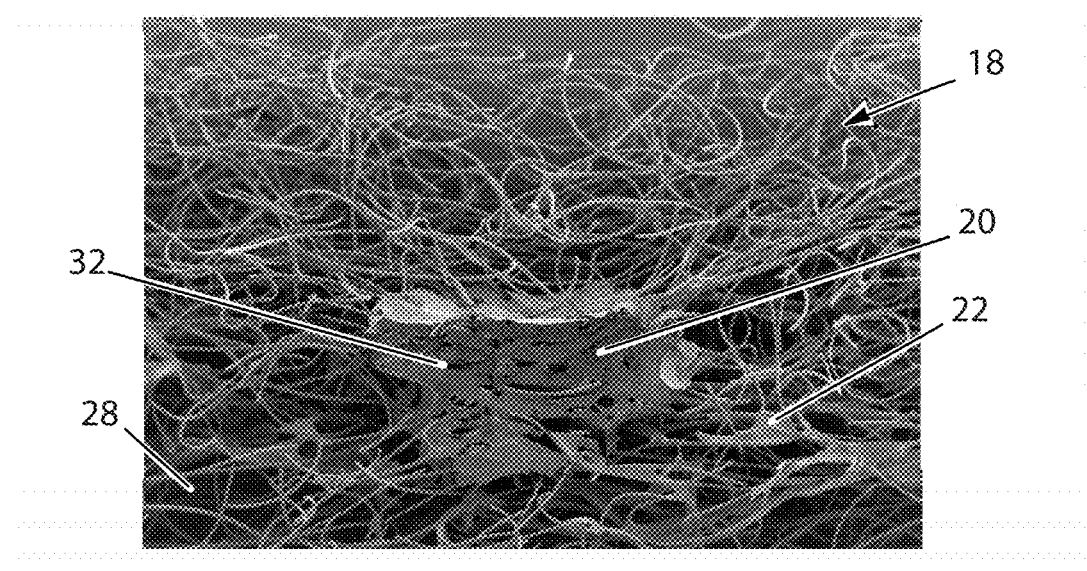
FIG. 15 is an SEM of a heterogeneous mass having an open-cell foam piece.

FIG. 15 shows another SEM micrograph of a heterogeneous mass 18 taken at a magnification of 18×. As shown in FIG. 15, the HIPE foam pieces 20 may be positioned below the outer surface of the heterogeneous mass 18 such that it does not form part of the outer surface of the heterogeneous mass 18 and is surrounded by fibers 22 and voids 28 containing gas. One or more vacuoles 32 may be formed within the foam piece 20.

Figure 16:
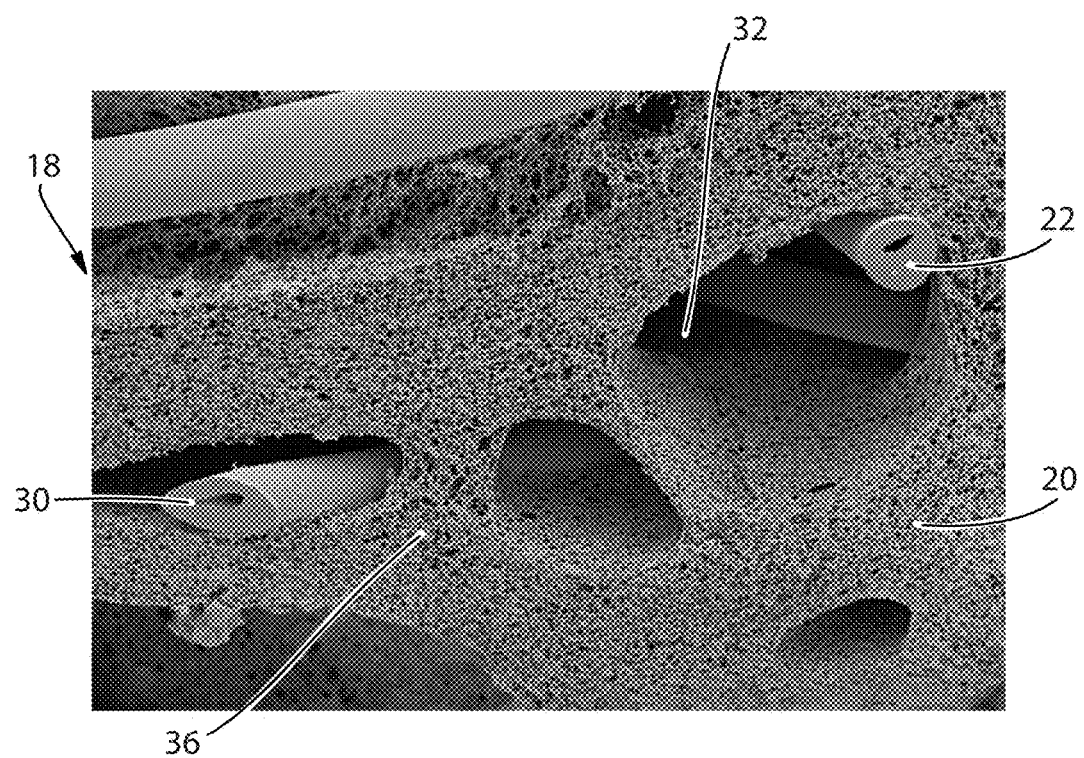
FIG. 16 is a magnified view of a portion of FIG. 15.
Figure 17:
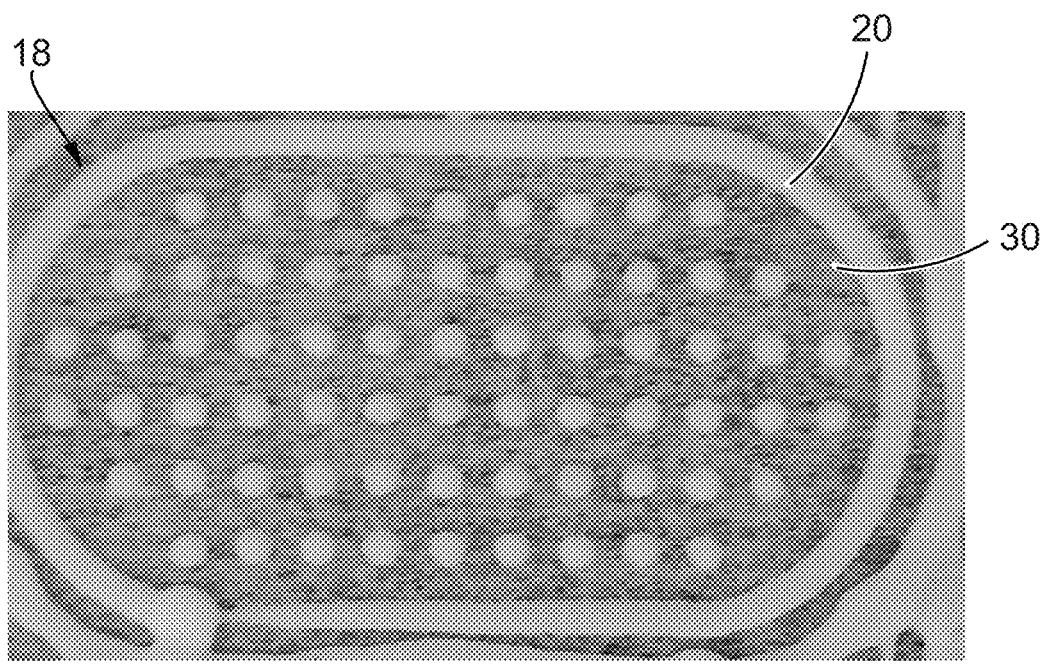
FIG. 17 is a top view image of a heterogeneous mass.

FIG. 16 shows a SEM micrograph of the heterogeneous mass of FIG. 15 taken at a magnification of 300×. As shown in FIG. 16, the heterogeneous mass 18 has an open-cell foam piece 20 that enrobes one or more enrobeable elements 30 in the form of fibers 22. As shown in FIG. 16, vacuoles 32 may exist within the enrobing foam 20. Vacuoles 32 may contain a portion of the enrobeable element 30. As shown in the figure, the vacuoles 32 have a cross-sectional surface area that is between 1.0002 and 900,000,000 times the cross-sectional surface area of the fibers 22 or between 1.26 and 9,000,000 times the cross-sectional surface area of the cells 36 in the open-cell foam piece 20. FIG. 17 is a photographic image of a heterogeneous mass 18 having enrobeable elements 30 comprising a nonwoven web and open-cell foam pieces 20 enrobing the enrobeable elements 30. As seen in the photographic image, the open-cell foam pieces are discrete along at least one of the lateral, longitudinal, or vertical axis of the heterogeneous mass. As seen in FIG. 17, the discrete open-cell foam pieces may form a pattern when viewed from above by a user.

A. An absorbent structure comprising one or more absorbent layers wherein the absorbent structure exhibits a first cycle Peak Force compression between about 30 grams and about 150 grams; wherein the absorbent structure further exhibits a fifth cycle dry recovery energy between 0.1 mJ and 2.8 mJ.

B. The absorbent structure according to paragraph A, wherein the absorbent structure exhibits a fifth cycle wet recovery energy between 0.6 mJ and 5.0 mJ.

C. The absorbent structure according to paragraph A or B, wherein the absorbent structure caliper change from Dry to Wet is between 0% and 175%.

D. The absorbent structure according to any of paragraphs A-C, wherein the absorbent structure exhibits an increase in Peak Force during a first cycle when measured from dry to wet.

E. The absorbent structure according to any of paragraphs A-D, wherein the absorbent structure comprises less than 30% fibers by volume.

F. An absorbent article comprising the absorbent structure according to any of paragraphs A-E.

G. The absorbent structure according to any of paragraphs A-D, wherein the absorbent structure comprises a layer of absorbent polymer material.

H. The absorbent structure according to paragraph G, wherein the layer of absorbent polymer material has a basis weight of less than 250 g/m$^2$.

I. The absorbent structure according to any of paragraphs A-H, wherein one or more layers of the absorbent structure are substantially free of cellulose fibers.
J. The absorbent structure according to any of paragraphs A-I, wherein the absorbent structure comprises a heterogeneous mass.
K. The absorbent structure according to paragraph J, wherein the heterogeneous mass comprises at least 5% of discrete open cell foam pieces for a fixed volume.
L. The absorbent structure according to any of paragraphs J-K, wherein the heterogeneous mass comprises enrobeable elements selected from the group consisting of creped cellulose wadding, fluffed cellulose fibers, wood pulp fibers also known as airfelt, textile fibers, synthetic fibers, rayon fibers, airlaid, absorbent fibers thermoplastic particulates or fibers, tricomponent fibers, bicomponent fibers, tufts, a nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, layered webs and combinations thereof.
M. The absorbent structure according to any of paragraphs J-L, wherein the heterogeneous mass comprises between 10% and 99% of gas for a fixed volume.
N. The absorbent structure according to paragraph K, wherein the discrete open cell foam pieces comprise HIPE foam.
O. The absorbent structure according to paragraph K, wherein the discrete open cell foam pieces are continuous along at least one of the longitudinal axis and the lateral axis.
P. An absorbent structure comprising one or more absorbent layers wherein the absorbent structure exhibits a first cycle Peak Force compression between about 30 grams and about 150 grams; wherein the absorbent structure further exhibits a fifth cycle dry recovery energy between 0.1 mJ and 2.8 mJ; and wherein the absorbent structure exhibits a fifth cycle wet recovery energy between 0.6 mJ and 5.0 mJ.
Q. The absorbent structure according to paragraph P, wherein the absorbent structure caliper change from Dry to Wet is between 0% and 175%.
R. The absorbent structure according to paragraph P or Q, wherein the absorbent structure exhibits an increase in Peak Force during a first cycle when measured from dry to wet.
S. The absorbent structure according to any of paragraphs P-R, wherein the absorbent structure comprises a layer of absorbent polymer material.
T. The absorbent structure according to any of paragraphs P-S, wherein the absorbent structure comprises a heterogeneous mass.

Method for Assessing Areas for Pore Size Calculations Using SEM Imaging:

Sample Preparation

The first step is to prepare the sample to be imaged using SEM: Section of the heterogeneous mass are cut into approximately 1.5 cm×4 cm strips from the original samples. These strips are then cut the strips into sections. Each section should contain the entire composite. The strips should be cut using a razor blade, such as VWR Single Edge Industrial, 0.009" thick surgical carbon steel or equivalent, at room temperature (available from VWR Scientific, Radnor, Pa. USA). Following the cutting of strips into sections, the sections are adhered to a mount using double-side Cu tape, with the-sectioned face up, and sputter Au coated.

Analysis

Secondary Electron (SE) images are obtained using an SEM, such as a FEI Quanta 450 (available from FEI Company, Hillsboro, Oreg., USA), operated in high-vacuum mode using acceleration voltages between 3 and 5 kV and a working distance of approximately 12-18 mm.

This methodology assumes the analyst is skilled in SEM operation so that images with sufficient contrast are obtained.

Viewing the SEM Sample

Samples should be viewed at 25 or 50× magnification. The different pore-size ranges are distinguished by the different portions within the heterogeneous mass. Distinct portions exhibit different cell/pore sizes/open area/solid phase vs gas phase. The magnification for the portions is chosen to enable clear visualization of the portion and the ability to distinguish the solid phase from the gas phase.

Determination of portions having different pore-size ranges is done at a magnification of 25×. The heterogeneous mass SEM is divided into an upper portion and a lower portion at the point where the lowest fiber is located along the Z-direction. Each portion is then divided into three portions. This creates three portions with the first upper portion and the first lower portion sharing a boundary. The pore-size range of the upper second portion is compared to pore-size range of the lower second portion. The lower third region may be compared to the upper second region and the lower second region to determine if there is an additional pore-size range. The upper third region may be compared to the upper second region and the lower second region to determine if there is an additional pore-size range. Pore size ranges are determined on the largest ten pores in the field of view and using software that is capable of analyzing the SEM images.

Bunch Compression Test

Bunched Compression of a sample is measured on a constant rate of extension tensile tester (a suitable instrument is the MTS Alliance using Testworks 4.0 software, as available from MTS Systems Corp., Eden Prairie, Minn., or equivalent) using a load cell for which the forces measured are within 10% to 90% of the limit of the cell. All testing is performed in a room controlled at 23° C.±3C° and 50%±2% relative humidity. The test can be performed wet or dry.

Figure 18:
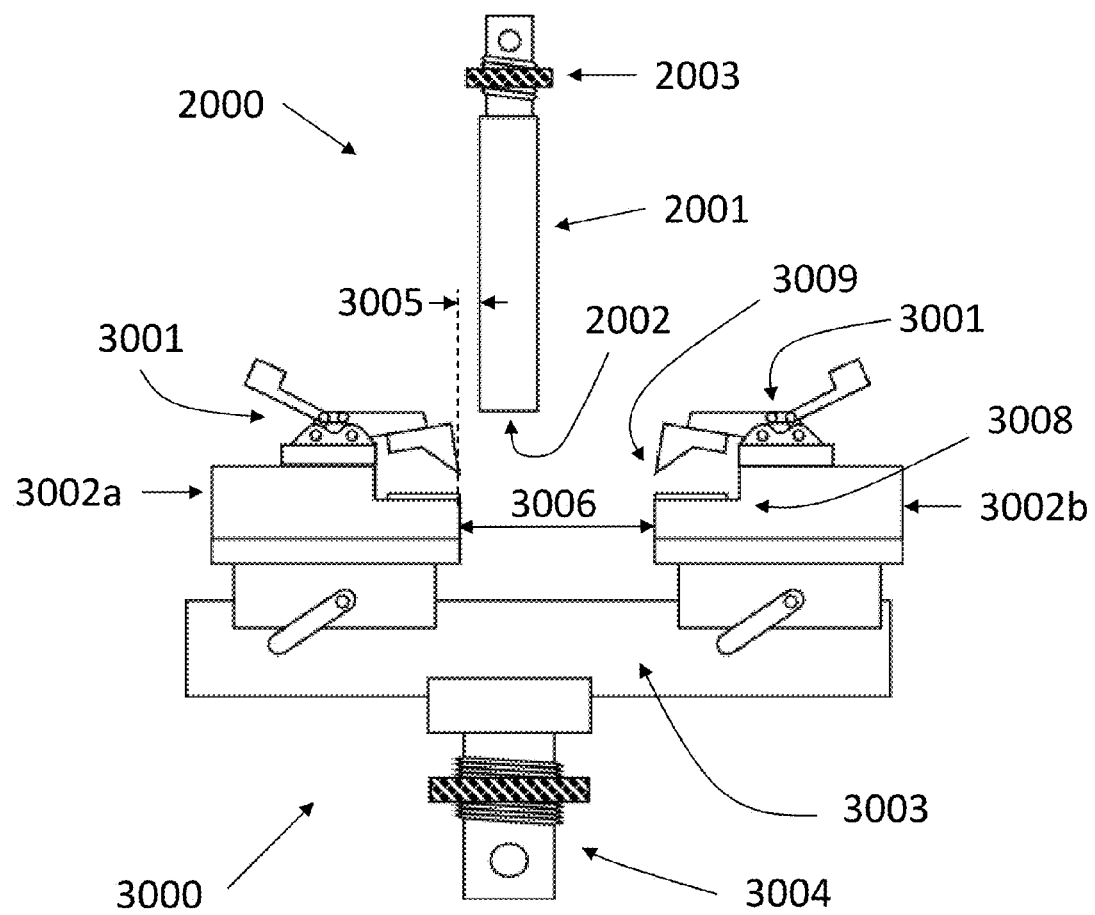
FIG. 18 is a schematic view of the equipment to perform the Bunch Compression test.

The bottom stationary fixture 3000 consists of two matching sample clamps 3001 each 100 mm wide each mounted on its own movable platform 3002a, 3002b. The clamp has a "knife edge" 3009 that is 110 mm long, which clamps against a 1 mm thick hard rubber face 3008 (as shown in FIG. 18). When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3C° and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines. The specimen can be analyzed both wet and dry. The dry specimen requires no further preparation. The wet specimens are dosed with one of two test solutions: 10.00 mL±0.01 mL of a 0.9% w/v saline solution (i.e., 9.0 g of NaCl diluted to 1 L deionized water) or 7.00 mL±0.01 mL 10% w/v saline solution (100.0 g of NaCl diluted to 1 L deionized water). The dose is added using a calibrated Eppendorf-type pipettor, spreading the fluid over the complete body facing surface of the specimen within a period of approximately 3 sec. The wet specimen is tested 15.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 19A:
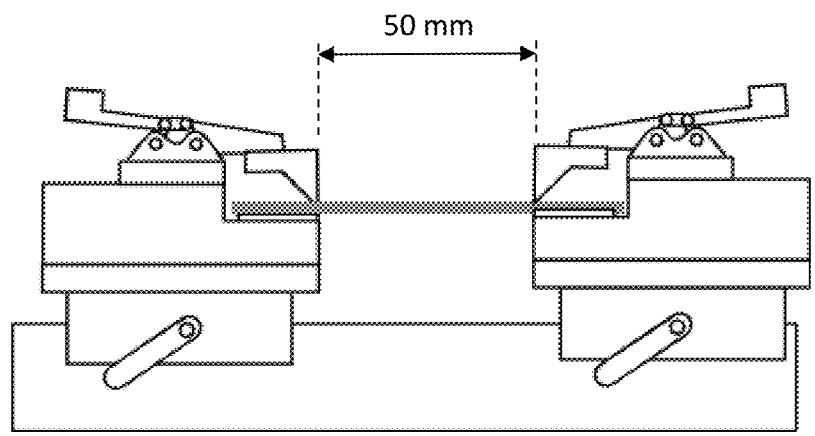
FIGS. 19a-b are a schematic view of the equipment to perform the Bunch Compression test.
Figure 19B:
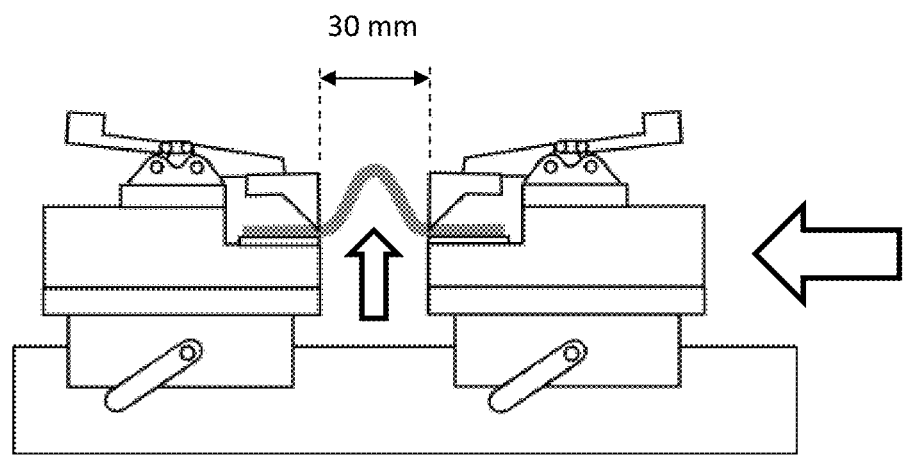

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps. Referring to FIG. 19a, place the specimen with its longitudinal edges (i.e., the 100 mm long edges) within the clamps. With the specimen laterally centered, securely fasten both edges. Referring to FIG. 19b, move the right platform 3002b toward the stationary platform 3002a a distance 20.0 mm Allow the specimen to bow upward as the movable platform is positioned. Manually lower the probe 2001 until the bottom surface is approximately 1 cm above the top of the bowed specimen.

Figure 20A:
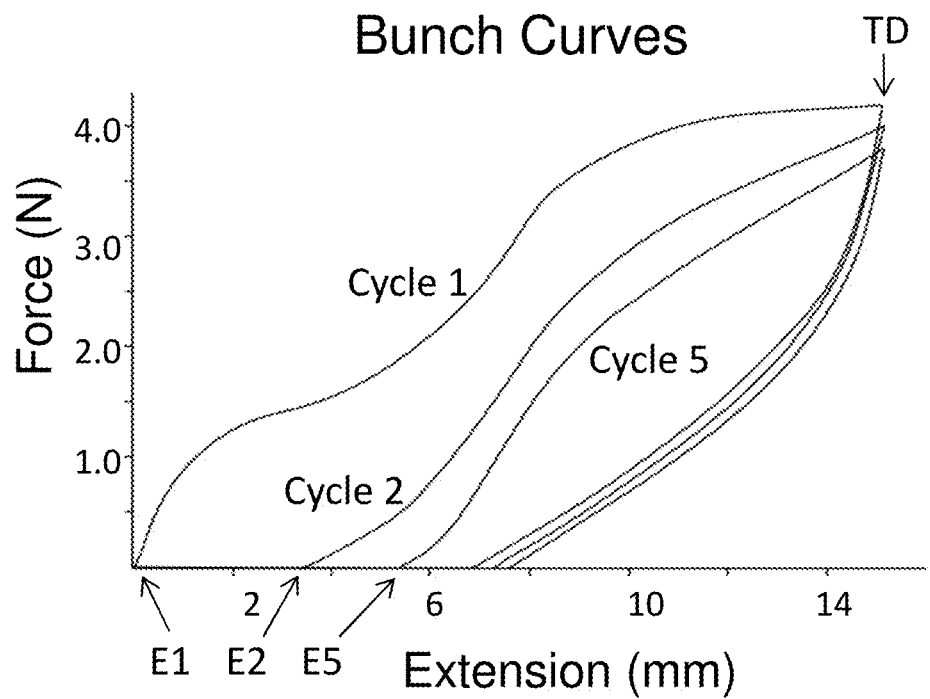
FIGS. 20a-b is a representative curve from the Bunch Compression test method.
Figure 20B:
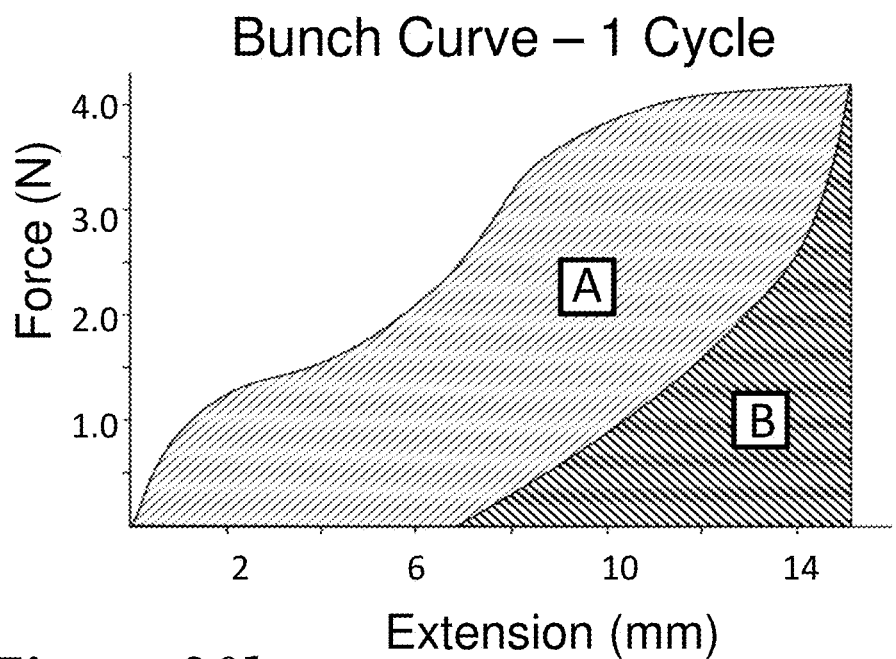

Start the test and collect displacement (mm) verses force (N) data for all five cycles. Construct a graph of Force (N) versus displacement (mm) separately for all cycles. A representative curve is shown in FIG. 20a. From the curve record the Maximum Compression Force for each Cycle to the nearest 0.01N. Calculate the % Recovery between the First and Second cycle as (TD-E2)/(TD-E1)*100 where TD is the total displacement and E2 is the extension on the second compression curve that exceeds 0.02 N. Record to the nearest 0.01%. In like fashion calculate the % Recovery between the First Cycle and other cycles as (TD-Ei)/(TD-E1)*100 and report to the nearest 0.01%. Referring to FIG. 20b, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion calculate the Energy of Compression (mJ), Energy Loss (mJ) and Energy of Recovery (mJ) for each of the other cycles and record to the nearest 0.1 mJ For each sample, analyze a total of five (5) replicates and report the arithmetic mean for each parameter. All results are reported specifically as dry or wet including test fluid (0.9% or 10%).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin, having a longitudinal axis and a transverse axis and comprising an absorbent core structure comprising one or more absorbent layers, the one or more absorbent layers comprising a heterogeneous mass, the heterogeneous mass comprising a nonwoven web of fibers and a plurality of discrete open cell foam pieces enrobing fibers within the nonwoven web, wherein the discrete open cell foam pieces are present and distributed among the fibers of the nonwoven web across and within at least a central region of the napkin occupying an intersection of the longitudinal axis and the transverse axis, and wherein the absorbent core structure exhibits a first cycle Peak Force compression between about 30 grams and about 150 grams; wherein the absorbent structure further exhibits a fifth cycle dry recovery energy between 0.1 mJ and 2.8 mJ.

2. The sanitary napkin of claim 1, wherein the absorbent core structure exhibits a fifth cycle wet recovery energy between 0.6 mJ and 5.0 mJ.

3. The sanitary napkin of claim 1, wherein the absorbent core structure caliper change from Dry to Wet is between 0% and 175%.

4. The sanitary napkin of claim 1, wherein the absorbent core structure exhibits an increase in Peak Force during a first cycle when measured from dry to wet.

5. The sanitary napkin of claim 1, wherein the absorbent core structure comprises less than 30% fibers by volume.

6. The sanitary napkin according to claim 1, wherein the absorbent core structure comprises a layer of absorbent polymer material.

7. The sanitary napkin according to claim 6, wherein the layer of absorbent polymer material has a basis weight of less than 250 g/m$^2$.

8. The sanitary napkin of claim 1, wherein one or more layers of the absorbent core structure are substantially free of cellulose fibers.

9. The sanitary napkin of claim 1, wherein the heterogeneous mass comprises at least 5% of discrete open cell foam pieces for a fixed volume.

10. The sanitary napkin of claim 9, wherein the discrete open cell foam pieces comprise HIPE foam.

11. The sanitary napkin of claim 9, wherein the discrete open cell foam pieces are continuous along at least one of the longitudinal axis and the transverse axis.

12. The sanitary napkin of claim 1, wherein the heterogeneous mass comprises enrobeable elements selected from the group consisting of creped cellulose wadding, fluffed cellulose fibers, wood pulp fibers also known as airfelt, textile fibers, synthetic fibers, rayon fibers, airlaid, absorbent fibers thermoplastic particulates or fibers, tricomponent fibers, bicomponent fibers, tufts, a nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, layered webs and combinations thereof.

13. The sanitary napkin of claim 1, wherein the heterogeneous mass comprises between 10% and 99% of gas for a fixed volume.

14. A sanitary napkin, having a longitudinal axis and a transverse axis and comprising an absorbent core structure comprising one or more absorbent layers, the one or more absorbent layers comprising a heterogeneous mass, the heterogeneous mass comprising a nonwoven web of fibers and a plurality of discrete open cell foam pieces enrobing fibers within the nonwoven web, wherein the discrete open cell foam pieces are present and distributed among the fibers of the nonwoven web across and within at least a central region of the napkin occupying an intersection of the longitudinal axis and the transverse axis, and wherein the absorbent core structure exhibits a first cycle Peak Force compression between about 30 grams and about 150 grams; wherein the absorbent core structure further exhibits a fifth cycle dry recovery energy between 0.1 mJ and 2.8 mJ; and wherein the absorbent structure exhibits a fifth cycle wet recovery energy between 0.6 mJ and 5.0 mJ.

15. The sanitary napkin of claim 14, wherein the absorbent structure caliper change from Dry to Wet is between 0% and 175%.

16. The sanitary napkin of claim 14, wherein the absorbent core structure exhibits an increase in Peak Force during a first cycle when measured from dry to wet.

17. The sanitary napkin according to claim 14, wherein the absorbent structure comprises a layer of absorbent polymer material.

* * * * *